United States Patent
Moe et al.

(10) Patent No.: US 9,464,122 B2
(45) Date of Patent: Oct. 11, 2016

(54) METHODS AND COMPOSITIONS COMPRISING TAU OLIGOMERS

(75) Inventors: James G. Moe, Stamford, CT (US); Eliot J. Davidowitz, West Hempstead, NY (US)

(73) Assignee: Oligomerix, Inc., New York, NY (US)

( * ) Notice: Subject to any disclaimer, the term of this patent is extended or adjusted under 35 U.S.C. 154(b) by 848 days.

(21) Appl. No.: 13/060,143

(22) PCT Filed: Aug. 21, 2009

(86) PCT No.: PCT/US2009/004776
§ 371 (c)(1),
(2), (4) Date: Sep. 9, 2011

(87) PCT Pub. No.: WO2012/054008
PCT Pub. Date: Apr. 26, 2012

(65) Prior Publication Data
US 2012/0029169 A1    Feb. 2, 2012

Related U.S. Application Data

(60) Provisional application No. 61/189,679, filed on Aug. 20, 2008.

(51) Int. Cl.
C07K 14/47    (2006.01)
A61K 38/17    (2006.01)
G01N 33/68    (2006.01)

(52) U.S. Cl.
CPC ........... C07K 14/47 (2013.01); A61K 38/1709 (2013.01); *G01N 2500/00* (2013.01); *G01N 2800/2821* (2013.01)

(58) Field of Classification Search
CPC ............. C07K 14/47; A61K 38/1709; G01N 2333/47
See application file for complete search history.

(56) References Cited

U.S. PATENT DOCUMENTS 6,200,768 B1 *    3/2001    Mandelkow et al. .......... 435/15
2007/0218491 A1 *    9/2007    Vasan ................ G01N 33/6896
                                                    435/6.16

OTHER PUBLICATIONS

Bhattacharya et al., Biochem. Biophys. Res. Comm., vol. 285, pp. 20-26, 2001.*

Ruben et al., JBC, vol. 266, 1991, pp. 22019-22027.*
Maeda S et al. Granular tau oligomers as intermediates of tau filaments. Biochem. 2007, 46:3856-3861.*
Tian, Huilai, et al. "Trimeric Tau is Toxic to Human Neuronal Cells at Low Nanomolar Concentrations," International Journal of Cell Biology, vol. 2013, Article ID 260787, 9 pages, Hindawi Publishing Corp.
Martin, Ludovic, et al. "Post-translational modifications of tau protein: Implications for Alzheimer's disease," Neurochemistry International, 58 (2011) 458-471.
Friedhoff, P., et al. "A nucleated assembly mechanism of Alzheimer paired helical filaments," Proc. Natl. Acad. Sci. USA, vol. 95, pp. 15712-15717, Dec. 1998.
Friedhoff, P., et al. "Rapid Assembly o fAlzheimer-like Paired He4lical Filaments from Microtubule-Associated Protein Tau Monitored by Fluorescence in Solution," Biochemistry 1998, 37, 10223-10230.
Liu, F., et al. "O-GlcNAcylation regulates phosphorylation of tau: A mechanism involved in Alzheimer's disease," PNAS, Jul. 20, 2004, vol. 101, No. 29, 10804-10809.
Yuzwa, S., et al. "Mapping O-GlcNAc modification sites on tau and generation of a site-specific O-GlcNAc tau antibody," Amino Acids (2011) 40:857-868.
Yuzwa, S., et al. "O-GlcNAc Modification of tau Directly Inhibits Its Aggregation without Perturbing the Conformational Properties of tau Monomers," J. Mol. Biol. (2014) 426, 1736-1752.
United States Patent and Trademark Office Guidelines on Nature-Based Products, 2015.

* cited by examiner

*Primary Examiner* — Kimberly A. Ballard
(74) *Attorney, Agent, or Firm* — Sorell, Lenna & Schmidt, LLP; William D. Schmidt, Esq.

(57) ABSTRACT

Tau protein has a causative role in Alzheimer's disease and multiple other neurodegenerative disorders exhibiting tau histopathology collectively termed tauopathies. The primary function of tau protein is to facilitate assembly and maintenance of microtubules in neuronal axons. In the disease process tau protein becomes modified, loses its affinity to microtubules and accumulates in the cell body where it forms aggregates. The large neurofibrillary tangles formed from tau protein assembled into filaments were thought to be the pathological structure of tau. However, more recent work indicates that smaller, soluble oligomeric forms of tau are best associated with neuron loss and memory impairment. Here, novel compositions of tau oligomers and novel mechanisms for tau oligomer nucleation, extension and termination are taught. Methods for producing and purifying these structures for the development of small molecule and immunotherapeutics as well as antibodies for biomarkers of neurodegenerative diseases are taught.

26 Claims, 25 Drawing Sheets

Figure 16.

4R Tau Microtubule Binding Domains

R1 (8 charged aa, overall +4)   R2 (8 charged aa, overall +4) R3 (7 charged aa, overall +4)
 - + + +     - ++    +  +- ++    ++ +- +      +    +  -  +       +++
QTAPVPMPDLKNVKSKIGSTENLKHQPGGGKVQIINKKLDLSNVQSKCGSKDNIKHVPGGGSVQIVYKPVDLSKVTSKCGSLGNIHHKPGGGQ
ppnnnnnnpnpnppppnnpppnnpppnnnnnpnpnppppnnpppnnpnpnppppnnpppnnpnpnppppnnnnp R4 (11 charged aa, overall +1)  R' (13 charged aa, overall +5)
 - + -+ - +-++    +   -   + +      ++ - ++ +-  ++ + + -+ -  +
VEVKSEKLDFKDRVQSKIGSLDNITHVPGGGNKKIETHKLTFRENAKAKTDHGAEIVYKSPVVS
npnppppnpnppnpnnpnppnnnnnpppnpppnpnpppnnpppnnpnpnppppnnnnp

Figure 24.

Peptide 1
H2N-GGGKVQIINKKLDLSNVQSKCGSKDNIKHV-COOH 30 amino acids

Peptide 2
H2N-GGGSVQIVYKPVDLSKVTSKCGSLGNIHH-COOH 29 amino acids

SEQUENCE LISTING

```
<160> NUMBER OF SEQ ID NOS: 7

<210> SEQ ID NO 1
<211> LENGTH: 352
<212> TYPE: PRT
<213> ORGANISM: Homo sapiens

<400> SEQUENCE: 1

Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Ala Glu Glu Ala
            35                  40                  45

Gly Ile Gly Asp Thr Pro Ser Leu Glu Asp Glu Ala Ala Gly His Val
        50                  55                  60

Thr Gln Ala Arg Met Val Ser Lys Ser Lys Asp Gly Thr Gly Ser Asp
    65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110
```

```
Ile Pro Ala Lys Thr Pro Pro Ala Pro Lys Thr Pro Ser Ser Gly
            115                 120                 125

Glu Pro Pro Lys Ser Gly Asp Arg Ser Gly Tyr Ser Ser Pro Gly Ser
130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
            195                 200                 205

Lys His Gln Pro Gly Gly Gly Lys Val Gln Ile Val Tyr Lys Pro Val
210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
            275                 280                 285

Phe Arg Glu Asn Ala Lys Ala Lys Thr Asp His Gly Ala Glu Ile Val
290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350

<210> SEQ ID NO 2
<211> LENGTH: 381
<212> TYPE: PRT
<213> ORGANISM: Homo sapiens

<400> SEQUENCE: 2

Met Ala Glu Pro Arg Gln Glu Phe Glu Val Met Glu Asp His Ala Gly
  1               5                  10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Ala Glu Glu Ala Gly Ile Gly
 65                 70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140
```

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Val Tyr Lys Pro Val Asp Leu Ser
                245                 250                 255

Lys Val Thr Ser Lys Cys Gly Ser Leu Gly Asn Ile His His Lys Pro
            260                 265                 270

Gly Gly Gly Gln Val Glu Val Lys Ser Glu Lys Leu Asp Phe Lys Asp
        275                 280                 285

Arg Val Gln Ser Lys Ile Gly Ser Leu Asp Asn Ile Thr His Val Pro
    290                 295                 300

Gly Gly Gly Asn Lys Lys Ile Glu Thr His Lys Leu Thr Phe Arg Glu
305                 310                 315                 320

Asn Ala Lys Ala Lys Thr Asp His Gly Ala Glu Ile Val Tyr Lys Ser
                325                 330                 335

Pro Val Val Ser Gly Asp Thr Ser Pro Arg His Leu Ser Asn Val Ser
            340                 345                 350

Ser Thr Gly Ser Ile Asp Met Val Asp Ser Pro Gln Leu Ala Thr Leu
        355                 360                 365

Ala Asp Glu Val Ser Ala Ser Leu Ala Lys Gln Gly Leu
    370                 375                 380

<210> SEQ ID NO 3
<211> LENGTH: 383
<212> TYPE: PRT
<213> ORGANISM: Homo sapiens

<400> SEQUENCE: 3

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Ala Glu Glu Ala
            35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
            165                 170                 175

Ser Pro Ser Ser Ala Lys Ser Arg Leu Gln Thr Ala Pro Val Pro Met
        180                 185                 190

Pro Asp Leu Lys Asn Val Lys Ser Lys Ile Gly Ser Thr Glu Asn Leu
    195                 200                 205

Lys His Gln Pro Gly Gly Gly Lys Val Gln Ile Ile Asn Lys Lys Leu
210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
        355                 360                 365

Thr Leu Ala Asp Glu Val Ser Ala Ser Leu Ala Lys Gln Gly Leu
    370                 375                 380

<210> SEQ ID NO 4
<211> LENGTH: 410
<212> TYPE: PRT
<213> ORGANISM: Homo sapiens

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Pro
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Glu Ala Gly Ile Gly Asp Thr
65                  70                  75                  80

Pro Ser Leu Glu Asp Glu Ala Ala Gly His Val Thr Gln Ala Arg Met
                85                  90                  95

Val Ser Lys Ser Lys Asp Gly Thr Gly Ser Asp Asp Lys Lys Ala Lys
            100                 105                 110

Gly Ala Asp Gly Lys Thr Lys Ile Ala Thr Pro Arg Gly Ala Ala Pro
        115                 120                 125

Pro Gly Gln Lys Gly Gln Ala Asn Ala Thr Arg Ile Pro Ala Lys Thr
    130                 135                 140

Pro Pro Ala Pro Lys Thr Pro Pro Ser Ser Gly Glu Pro Pro Lys Ser
145                 150                 155                 160

Gly Asp Arg Ser Gly Tyr Ser Ser Pro Gly Ser Pro Gly Thr Pro Gly
                165                 170                 175

Ser Arg Ser Arg Thr Pro Ser Leu Pro Thr Pro Pro Thr Arg Glu Pro
            180                 185                 190

Lys Lys Val Ala Val Val Arg Thr Pro Pro Lys Ser Pro Ser Ser Ala
        195                 200                 205

Lys Ser Arg Leu Gln Thr Ala Pro Val Pro Met Pro Asp Leu Lys Asn
    210                 215                 220

Val Lys Ser Lys Ile Gly Ser Thr Glu Asn Leu Lys His Gln Pro Gly
225                 230                 235                 240

Gly Gly Lys Val Gln Ile Ile Asn Lys Lys Leu Asp Leu Ser Asn Val
                245                 250                 255

Gln Ser Lys Cys Gly Ser Lys Asp Asn Ile Lys His Val Pro Gly Gly
            260                 265                 270

Gly Ser Val Gln Ile Val Tyr Lys Pro Val Asp Leu Ser Lys Val Thr
        275                 280                 285

Ser Lys Cys Gly Ser Leu Gly Asn Ile His His Lys Pro Gly Gly Gly
    290                 295                 300

Gln Val Glu Val Lys Ser Lys Leu Asp Phe Lys Asp Arg Val Gln
305                 310                 315                 320

Ser Lys Ile Gly Ser Leu Asp Asn Ile Thr His Val Pro Gly Gly Gly
                325                 330                 335

Asn Lys Lys Ile Glu Thr His Lys Leu Thr Phe Arg Glu Asn Ala Lys
            340                 345                 350

Ala Lys Thr Asp His Gly Ala Glu Ile Val Tyr Lys Ser Pro Val Val
        355                 360                 365

Ser Gly Asp Thr Ser Pro Arg His Leu Ser Asn Val Ser Ser Thr Gly
    370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
                405                 410

<210> SEQ ID NO 5
<211> LENGTH: 412
<212> TYPE: PRT
<213> ORGANISM: Homo sapiens

<400> SEQUENCE: 5

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Pro
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Ala Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

```
Ala Lys Gly Ala Asp Gly Lys Thr Lys Ile Ala Thr Pro Arg Gly Ala
            115                 120                 125

Ala Pro Pro Gly Gln Lys Gly Gln Ala Asn Ala Thr Arg Ile Pro Ala
130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
195                 200                 205

Ser Ala Lys Ser Arg Leu Gln Thr Ala Pro Val Pro Met Pro Asp Leu
            210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
            260                 265                 270

Gly Gly Gly Ser Val Gln Ile Val Tyr Lys Pro Val Asp Leu Ser Lys
            275                 280                 285

Val Thr Ser Lys Cys Gly Ser Leu Gly Asn Ile His His Lys Pro Gly
            290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
            340                 345                 350

Ala Lys Ala Lys Thr Asp His Gly Ala Glu Ile Val Tyr Lys Ser Pro
            355                 360                 365

Val Val Ser Gly Asp Thr Ser Pro Arg His Leu Ser Asn Val Ser Ser
370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410

<210> SEQ ID NO 6
<211> LENGTH: 441
<212> TYPE: PRT
<213> ORGANISM: Homo sapiens

<400> SEQUENCE: 6

Met Ala Glu Pro Arg Gln Glu Phe Glu Val Met Glu Asp His Ala Gly
  1               5                  10                  15

Thr Tyr Gly Leu Gly Asp Arg Lys Asp Gln Gly Gly Tyr Thr Met His
             20                  25                  30

Gln Asp Gln Glu Gly Asp Thr Asp Ala Gly Leu Lys Glu Ser Pro Leu
         35                  40                  45

Gln Thr Pro Thr Glu Asp Gly Ser Glu Glu Pro Gly Ser Glu Thr Ser
     50                  55                  60
```

```
Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
             85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
            130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
            165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
            290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
            325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
            370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
            405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
            435                 440

<210> SEQ ID NO 7
<211> LENGTH: 42
<212> TYPE: PRT
<213> ORGANISM: Homo sapiens
```

```
<400> SEQUENCE: 7

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala
            35              40
```

METHODS AND COMPOSITIONS COMPRISING TAU OLIGOMERS

This application claims the benefit of the filing date of U.S. Provisional Application No. 61/189,679, filed Aug. 20, 2008, entitled "Methods And Composition Comprising Tau Oligomers." The entire disclosure is hereby incorporated by reference into the present disclosure.

This invention was made with Government support under Grant Nos. AG029777 and AG033474 awarded by the National Institutes of Health. The Government has certain rights in this invention.

BACKGROUND

Alzheimer's disease (AD) is the most common cause of dementia in the elderly that affects an estimated 15 million people worldwide and 40% of the population above 85 years. The disease is characterized by progressive loss of memory, speech and movement with a total incapacitation of the patient and eventually death. AD takes a terrible toll on those with the disease as well as their families, friends and caregivers.

The symptoms of AD manifest slowly and the first symptom may only be mild forgetfulness. In this stage, individuals may forget recent events, activities, the names of familiar people or things and may not be able to solve simple math problems. As the disease progresses into moderate stages of AD, symptoms are more easily noticed and become serious enough to cause people with AD or their family members to seek medical help. Moderate-stage symptoms of AD include forgetting how to do simple tasks such as grooming, and problems develop with speaking, understanding, reading, or writing. Severe stage AD patients may become anxious or aggressive, may wander away from home and ultimately need total care.

No cure is currently available for AD. Today, medication therapy focuses on controlling the symptoms of AD and its various stages. For example, mild to moderate AD can involve treatment with cholinesterase inhibitors such as Cognex® (tacrine), Aricept® (donepezil), Exelon® (rivastigmine), or Razadyne® (galantamine). Whereas moderate to severe AD can be treated with Namenda® (memantine). These medications may help delay or prevent AD symptoms from becoming worse for a limited period of time. So early AD treatment is warranted. However, there is no clear evidence that these medications have any effect on the underlying progression of the disease.

There is a large and rapidly growing unmet need for disease modifying drugs for Alzheimer's disease (AD). The classical hallmarks of AD are inter-neuronal plaques consisting of precipitates or aggregates of amyloid beta protein (Aβ), and intra-neuronal neurofibrillary tangles (NFTs) of tau protein. Tau protein promotes microtubule assembly and stability and is critical for the function of axons, whereas the normal function of Aβ is not fully understood. The amyloid cascade hypothesis has been widely accepted as the pathological pathway of AD. It holds that the generation of Aβ and accumulation of Aβ aggregates in the brain initiate the disease process. It is supported by genetic evidence that mutations leading to increased accumulation of Aβ aggregates leads to familial AD. However, there are a number of weaknesses in the Aβ cascade hypothesis in that it does not address the importance of other pathways that can cause neurodegeneration (Seabrook et al. 2007). The accumulation and distribution of NFTs in the brains of AD patients is highly correlated with disease progression and can be used to stage AD by post-mortem brain histopathology, whereas there is poor correlation between AD and the accumulation of neuritic plaques composed of beta amyloid. This has been used to challenge the amyloid hypothesis (Josephs et al. 2008). Lackluster results for Aβ directed therapeutics in late stage clinical trials has increased interest in exploring alternative targets for drug discovery such as tau (Iqbal et al. 2009).

While extensive research in the past decade has identified possible biomarkers for AD, there is still an urgent need for composition and methods that are specifically useful in diagnosing, stratifying, or monitoring the progression or regression of AD. New compositions and methods are also needed that serve as drug targets for the identification of new medication therapies to treat AD and to monitor different medications therapeutic effect when used to treat AD, as well as compositions that are useful as immunotherapeutic agents.

SUMMARY

The present application provides methods and compositions comprising tau oligomer or a fragment or peptide derivative thereof. These tau oligomers, fragments or peptide derivatives thereof can be used in diagnostic and prognostic assays, allowing AD to be diagnosed earlier (while the patient is alive) and more accurately than was previously possible. These tau oligomers, fragments or peptide derivatives thereof can better help the clinician stratify, or monitor the progression or regression of AD, than currently available assays. In addition, tau oligomers, fragments or peptide derivatives thereof identified according to the composition and methods disclosed can serve as drug targets for the identification of new therapeutic agents for the treatment of AD or other tauopathies and monitor different medication therapies benefit when used to treat AD or other tauopathies. In some embodiments, these tau oligomers, fragments or peptide derivatives thereof can be used as immunotherapeutic agents to stimulate the immune system.

In some embodiments, there is a novel model for tau oligomerization that provides novel compositions of tau oligomers that help teach how the relative overexpression of 4R tau can facilitate tau aggregation and neurodegenerative disease and how these structures may be used for discovery of small molecule drugs, immunotherapeutics and biomarkers for neurodegenerative diseases.

In one embodiment, a composition comprising stabilized tau oligomer or a fragment or peptide derivative thereof.

In another embodiment, a composition is provided, wherein (i) the tau oligomer is in at least one conformation comprising tau dimer, tau trimer, tau tetramer, tau pentamer, tau hexamer, tau septamer, tau octamer, tau nonamer, tau decamer, tau unadecamer, tau dodecamer, 3R tau, 4R tau, or mixtures of 3R tau and 4R tau or a fragment or peptide derivative thereof or a combination thereof; or (ii) the tau monomeric unit comprises one of SEQ ID NO. 1-6; or (iii) the tau oligomer is stable for at least 2 months; or (iv) the tau oligomer is substantially purified and/or isolated.

In some embodiments, a method is provided for screening an agent for modulation or disruption of purified tau dimer, tau trimer, tau tetramer, tau pentamer, tau hexamer or a combination thereof, the method comprising: a) contacting a sample containing tau dimer, tau trimer, tau tetramer, tau pentamer, tau hexamer or a combination thereof with an agent suspected of being capable of modulating tau oligomer formation or disrupting tau oligomers; and b) detecting the amount of tau dimer, tau trimer, tau tetramer, tau pentamer, tau hexamer or a combination thereof, wherein a decrease in tau dimer, tau trimer, tau tetramer, tau pentamer, tau hexamer or a combination thereof indicates that the agent modulates tau oligomer formation or disrupts tau oligomer.

In some embodiments, a composition is provided comprising a tau dimer, which comprises tau 4R-tau 4R dimer, tau 3R-4R tau dimer, or tau 3R-tau 3R dimer.

In some embodiments, a compound is provided that prevents tau-tau binding resulting from hydrogen bonding, van der Waals interaction such that disulfide bond formation is inhibited or prevented.

In some embodiments, a method is provided for screening an agent for modulation or disruption of tau oligomer, wherein the agent comprises curcumin, demethoxycurcumin, bis-demethoxycurcumin, and/or morin.

In some embodiments, a method is provided for screening an agent for modulation or disruption of tau oligomer, wherein the agent disrupts tau-tau oligomerizations by inhibiting tau-tau binding.

In some embodiments, a tau oligomer composition is provided comprising tau monomer units bound to each other by one or more disulfide bonds.

In some embodiments, a tau oligomer composition is provided, wherein the tau oligomer is tau dimer bound to each other by intermolecular disulfide bonds.

In some embodiments, a tau oligomer composition is provided, wherein the tau oligomer is tau dimer bound to each other by intermolecular disulfide bonds and the tau dimer has 3 or 4 microtubule binding repeat regions.

In some embodiments, a tau oligomer composition is provided comprising one or more fragments of tau comprising R2 R3-R3, or R3-R3, or R2R3-R2R3 complexes held together by one or more intermolecular disulfide bonds.

In some embodiments, a reagent composition is provided comprising a predetermined ratio of tau 3R to tau 4R used to generate tau oligomers of from about two to about twelve tau monomer units.

In some embodiments, a reagent composition is provided used to identify a pathological binding partner associated with AD or tauopathies.

In some embodiments, a reagent composition is provided used to perform high resolution NMR, X-ray crystallography, generating antibodies to specific oligomer sizes, or for immunotherapy.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

does not aggregate, and lane 5 the C-terminal fragment (amino acids 185-441) that contains the full 4R microtubule binding domain.

Figure 10:
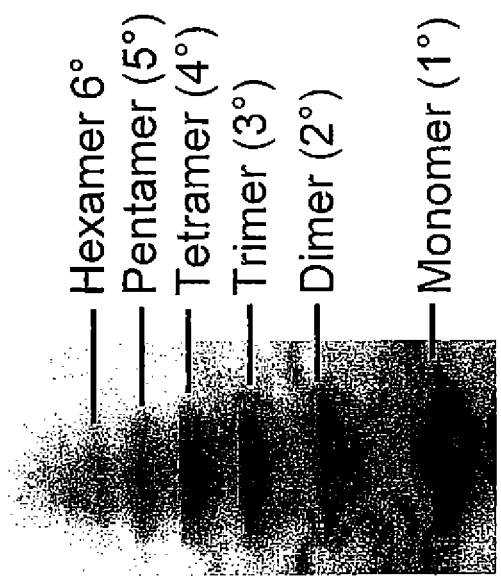

FIG. 10 illustrates that polymerization of tau oligomers occurs by addition of monomeric tau to a growing chain resulting in progressively longer tau oligomers as shown for tau441. Evidence for oligomer building via addition of monomer tau based on accumulation of lower order structures followed by higher order structures as shown. Furthermore, purified monomer is able to form dimers, whereas purified dimer and trimer do not show any higher order oligomers after 2 months at 4° C.

Figure 11:
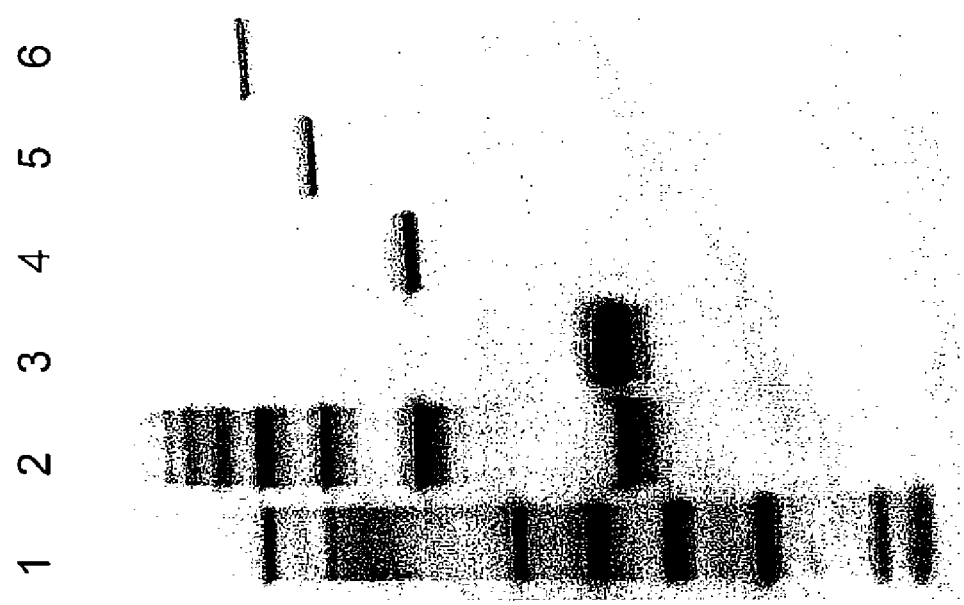

FIG. 11 illustrates that tau oligomers can be purified in stable form as shown for a mixture of tau412 oligomers that was purified. To prepare specific tau oligomers at high purification Tau412 oligomer enriched preparations (lane 2) were size-fractionated to isolate monomer (lane 3), dimer (lane 4), trimer (lane 5) and tetramer (lane 6) and stabilized in buffer.

Figure 12:
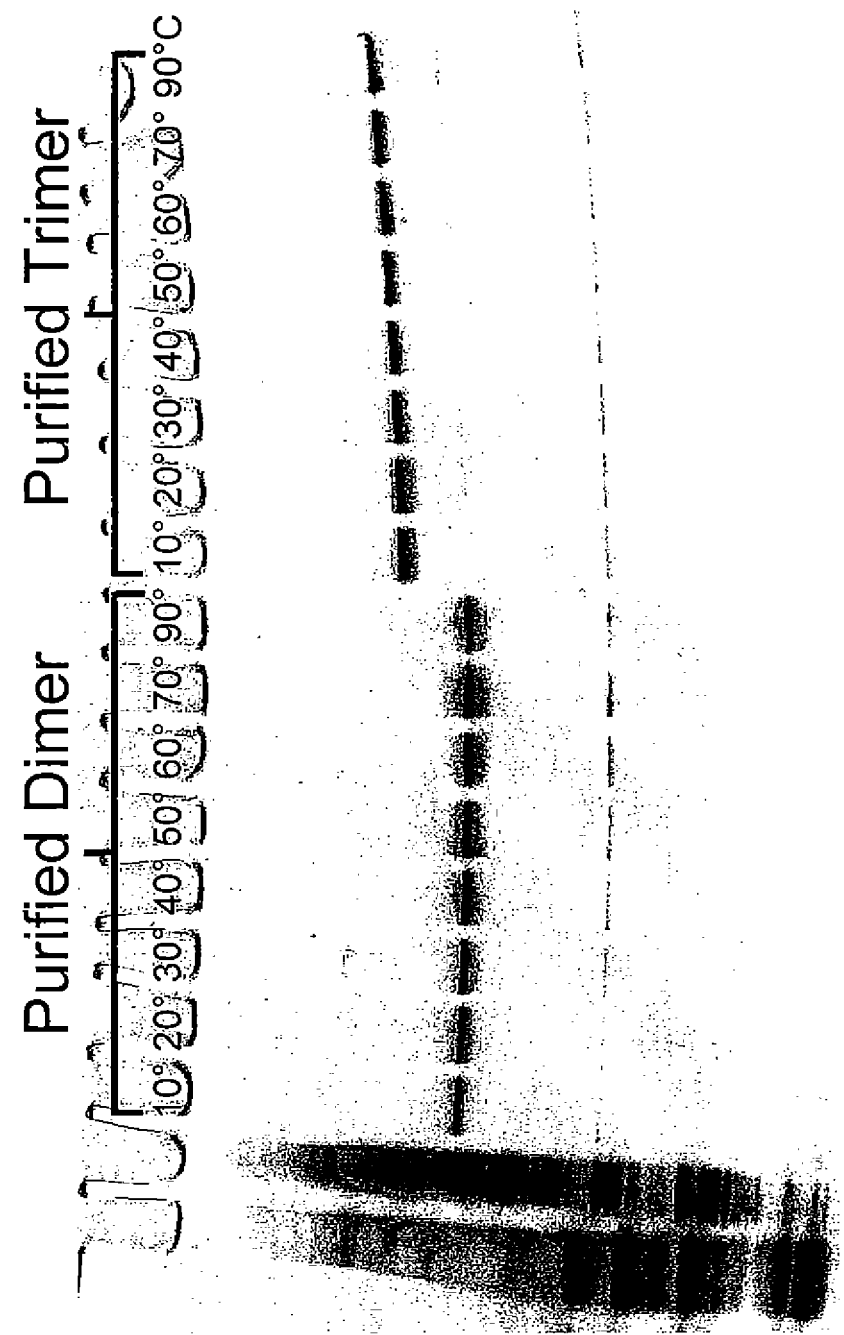

FIG. 12 illustrates that disulfide mediated tau oligomers have high thermal stability up to 90° C.

Figure 13:
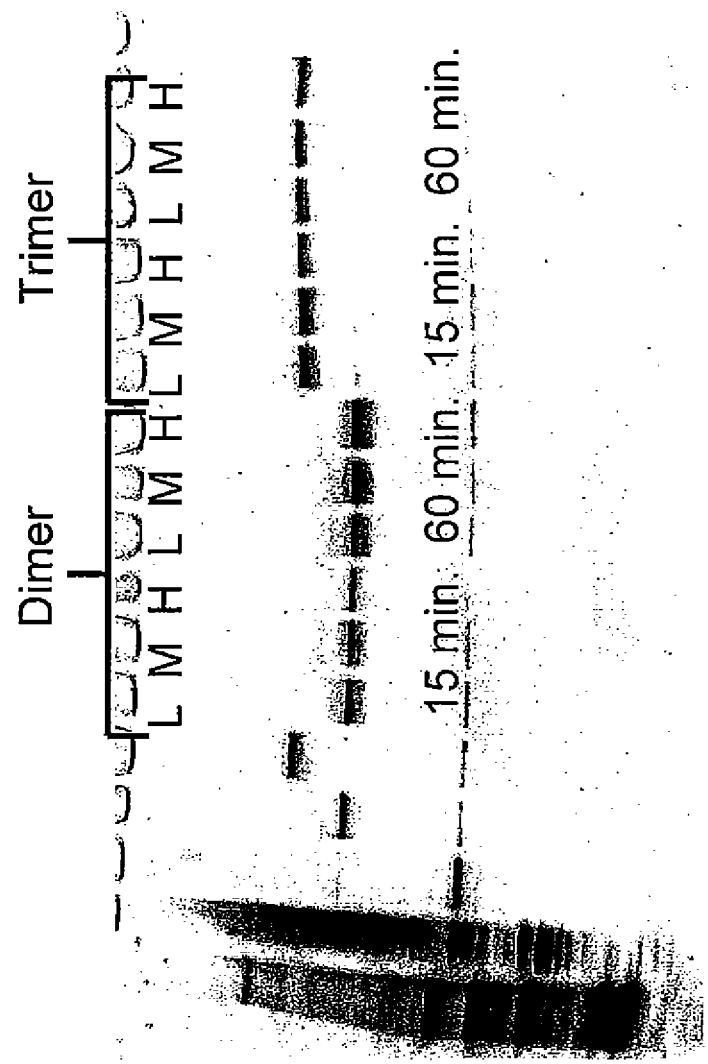

FIG. 13 illustrates that tau oligomers are highly stabile under high salt conditions at 37° C. Tau441 where L—low salt; M—medium salt; and H—high salt.

Figure 14:
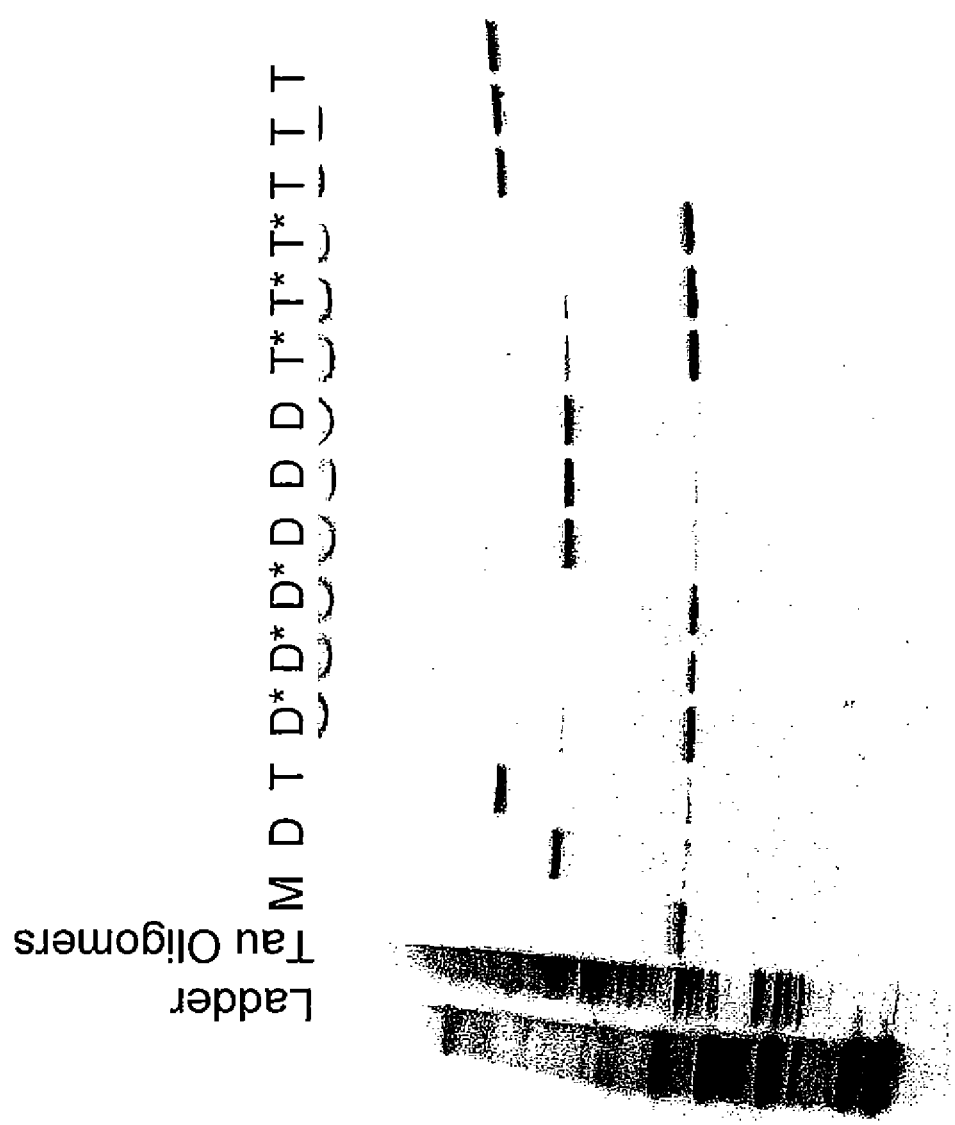

FIG. 14 illustrates the temperature stability of tau441 oligomers and purified dimer and trimer with and without reducing agent (DTT) Both the dimer and trimer show good stability at 37° C. (incubated at 15, 30 and 60 minutes) Dimer formation—dependent on the formation of one or more disulfide bonds. Trimer formation—demonstrates at least one thiol group is available in the dimer M—purified monomer D is purified dimer; D* is purified dimer plus reducing agent; T—purified trimer; and T*—purified trimer plus reducing agent.

Figure 15:
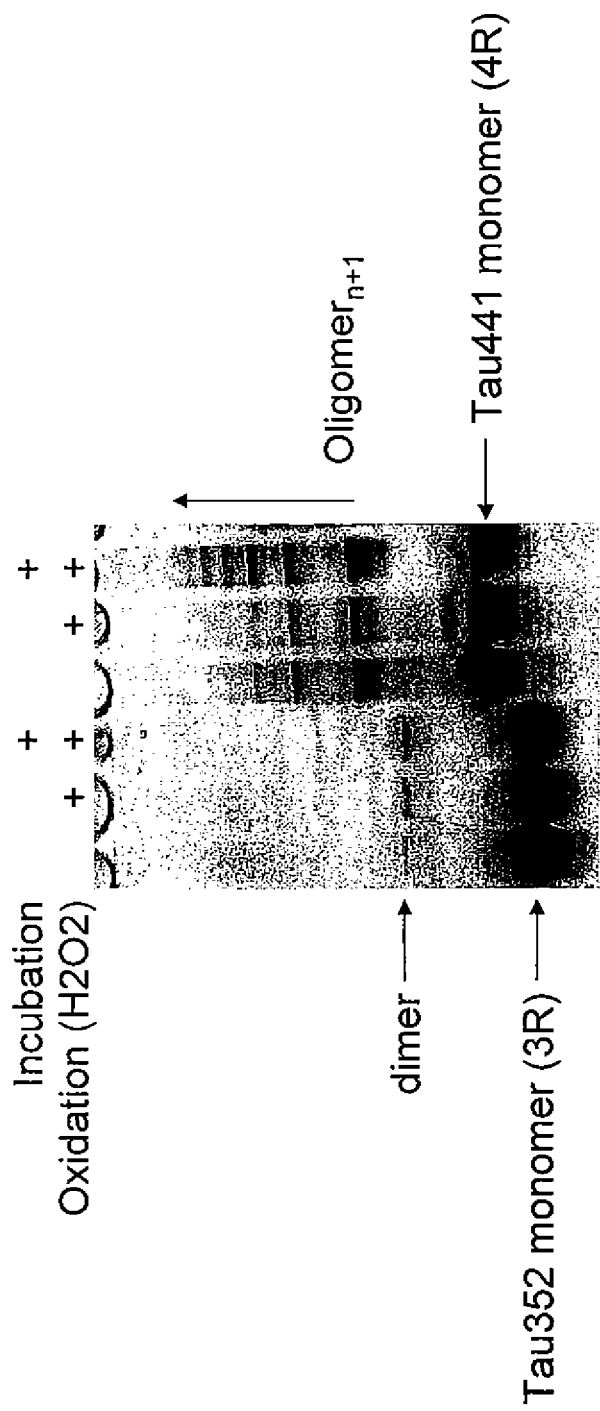

FIG. 15 illustrates intrinsic differences in tau isoform oligomerization that provides the basis for the disulfide mediated tau oligomer model. 3R tau can only form dimers and has a single cysteine (Cys322); whereas 4R tau forms n+1 oligomers without termination and has two cysteines (Cys291 and Cys322). Oxidative conditions caused rapid oligomer formation due to oxidation of free thiols in monomeric tau.

FIG. 16 illustrates microtubule binding domain structural features through the repeat and pseudo repeat regions. The amino acid charge is indicated above the amino acid abbreviation. The beta-sheet forming regions and cysteines are highlighted in bold. Potential proline or glycine mediated bending regions are underlined. The microtubule binding regions are defined as follows: R1=Q244 to K274; R2=V275 to S305; R3=V306 to Q336; R4=V337 to N368; and R'=K369 to S400. In 3R tau isoforms, R2 is absent.

Figure 17:
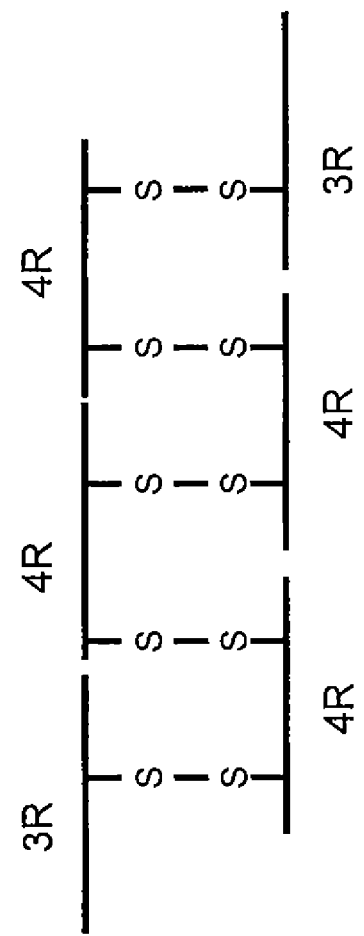

FIG. 17 illustrates the model for formation of disulfide mediated tau oligomers. For 4R tau protein isoforms, there are two cysteines and reaction with monomer or oligomer leaves a free thiol available for reaction. For 3R tau protein isoforms, there is a single cysteine which terminates a growing oligomer chain. In healthy brains, the ratio of 3R/4R isoforms is approximately 1.0; whereas in AD Brains the ratio of 3R/4R is approximately 0.2-0.3.

Figure 18:
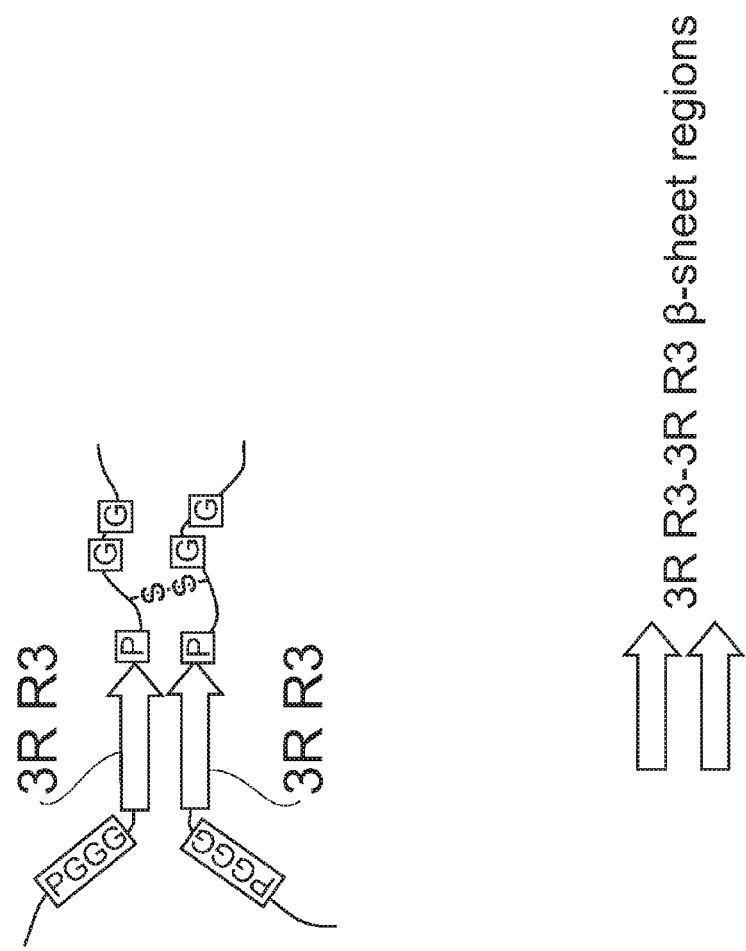

FIG. 18 illustrates the model of a disulfide mediated structure for a 3R/3R tau dimer showing alignment of the peptides in parallel to form a beta sheet structure.

Figure 19:
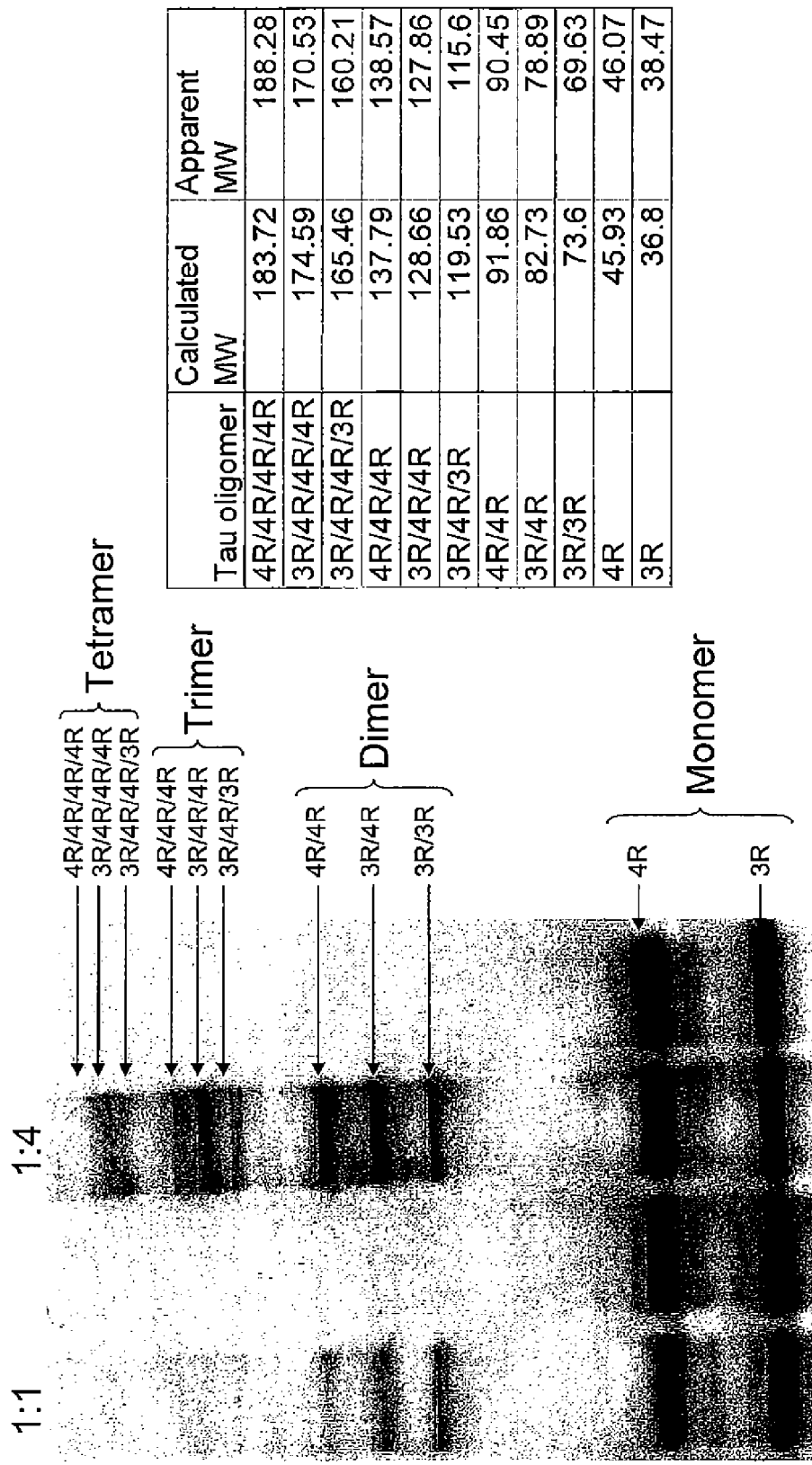

FIG. 19 illustrates the tau oligomers formed using various ratios of 3R to 4R tau protein isoforms during reaction. The accumulation of higher order aggregates indicates that the dimer is reactive consistent with the formation of only a single disulfide in the initial 4R/4R structure. Incorporation of 3R tau limits oligomer extension. Higher order oligomers formed with increased levels of 4R tau. The table shows the calculated and apparent molecular weight for the 3R/3R 4R/4R and 3R and 4R tau oligomers formed.

Figure 20:
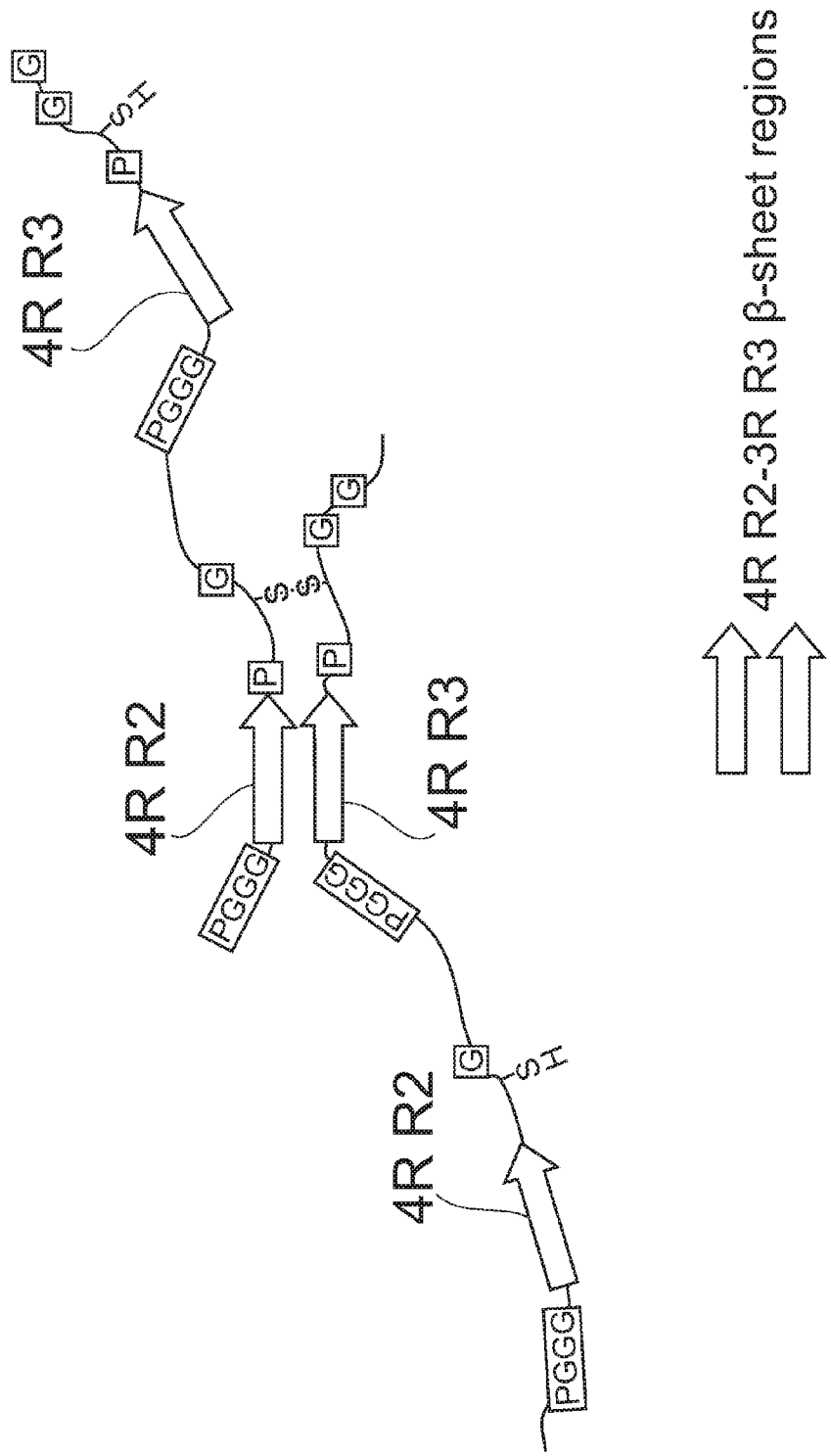

FIG. 20 illustrates the model of a disulfide mediated structure for a 4R/4R tau dimer showing alignment of the peptides in parallel to form a beta sheet. The formation of an intermolecular disulfide linkage traps the tau proteins into an aggregation template that contains two reactive free thiol groups.

Figure 21:
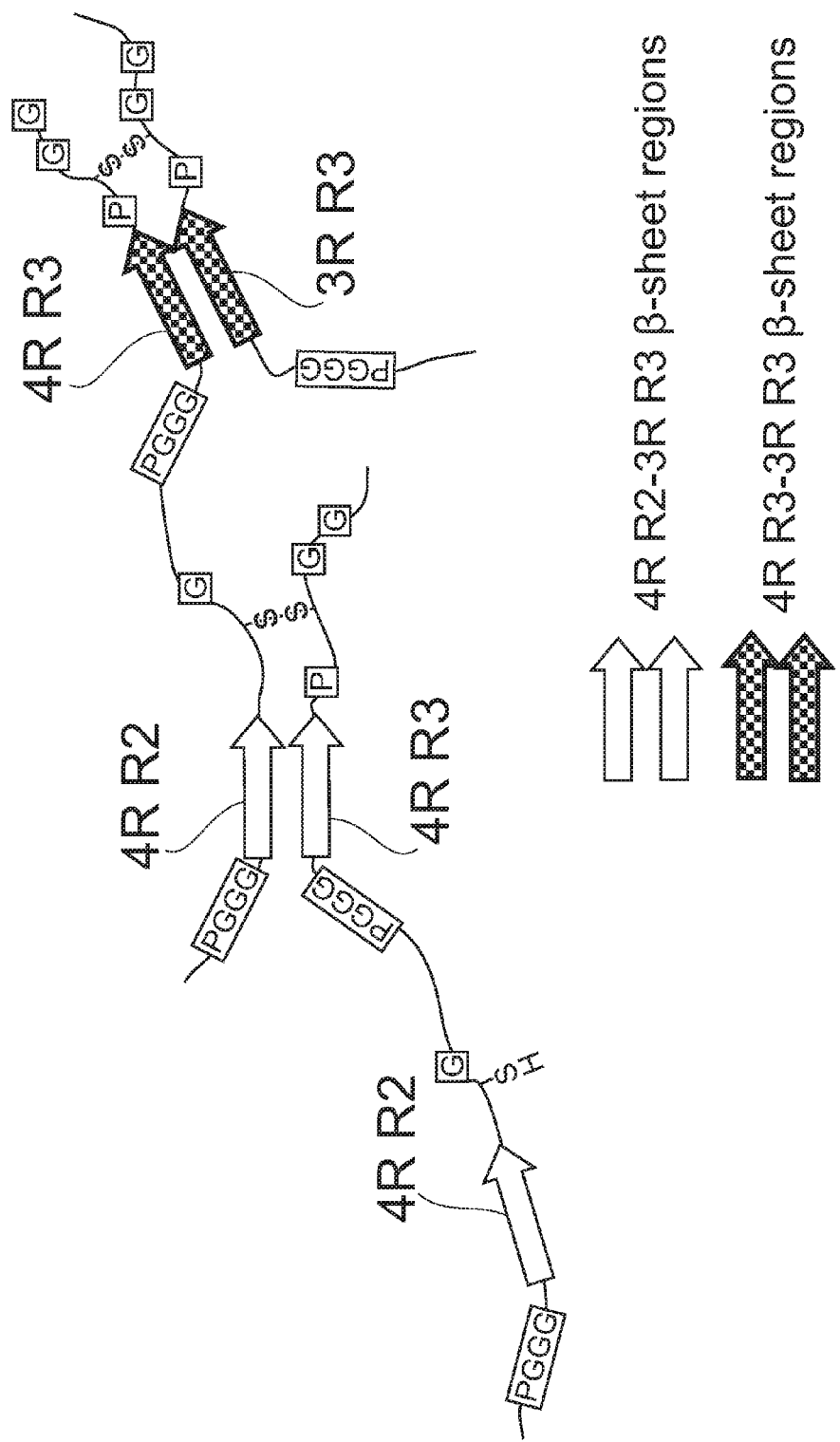

FIG. 21 illustrates the model of a disulfide mediated structure for a 4R/4R/3R tau trimer showing alignment of the peptides in parallel to form a beta sheet. The reaction of 3R tau protein to the 4R/4R tau dimer eliminates occurs via additional formation of a disulfide linkage. This results in the case of the 4R/4R/3R tau trimer with a single remaining reactive free thiol group. At this time, there is no way to predict whether the disulfide is between 3R R3 and 4R R2 or 4R R3. The trimer is shown with the disulfide linkage to 4R R3 strictly for illustrative purposes.

Figure 22:
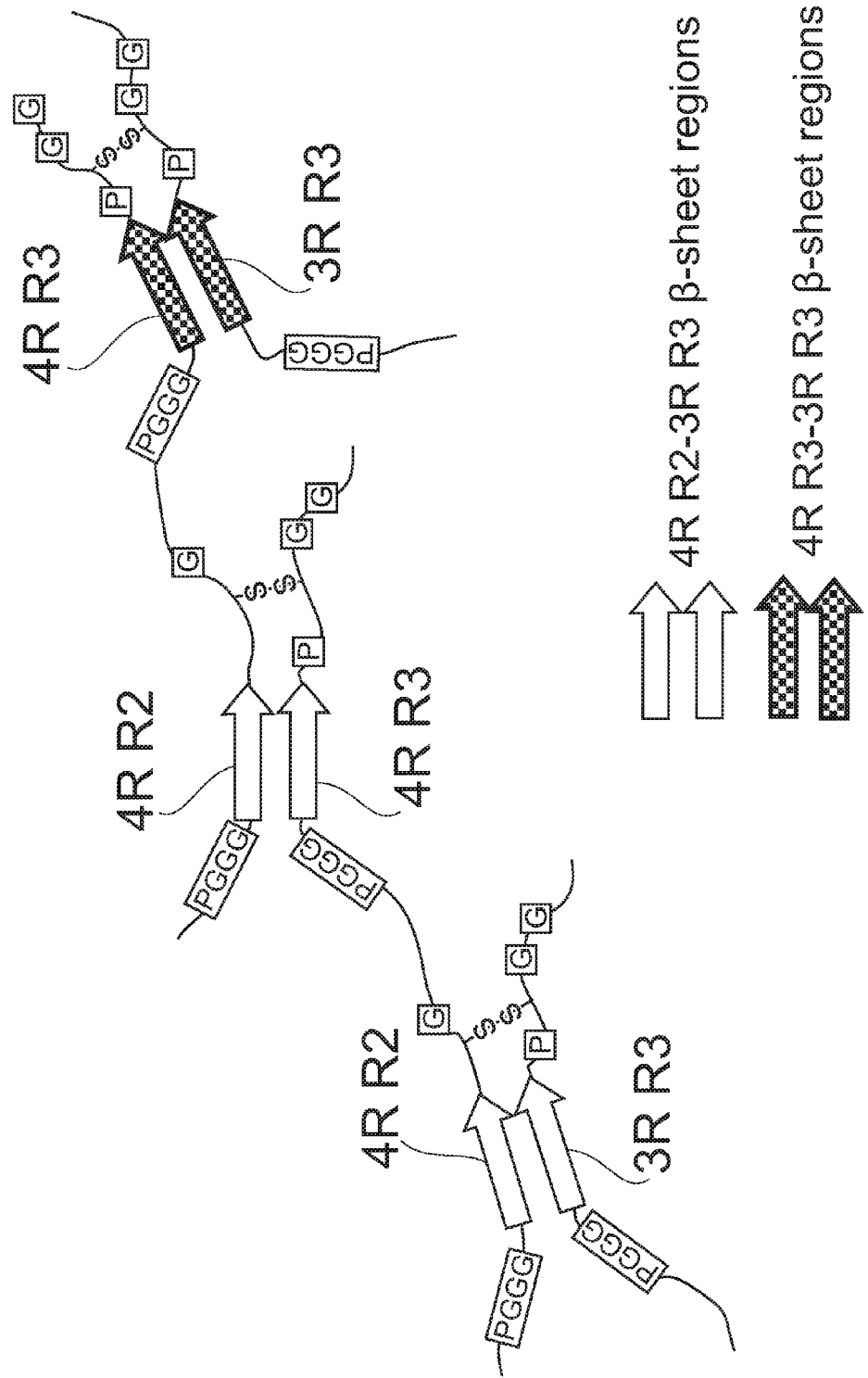

FIG. 22 illustrates the model of a disulfide mediated structure for a 3R/4R/4R/3R tau tetramer, showing alignment of the peptides in parallel to form an additional beta sheet structure. The 3R/4R/4R/3R tau tetramer contains no reactive free thiol groups and cannot propagate disulfide mediated tau oligomers.

Figure 23:
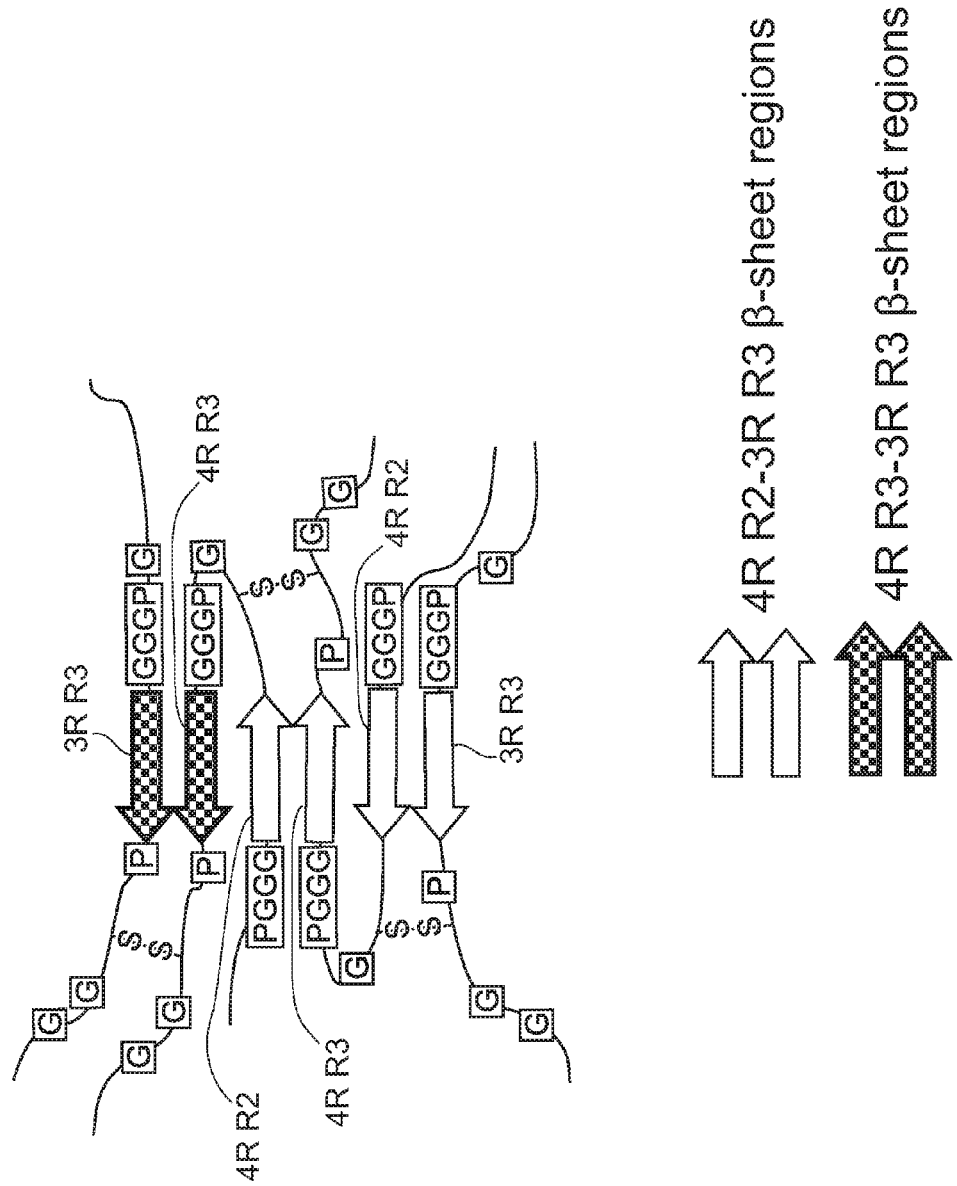

FIG. 23 illustrates a stacked tau tetramer structure (3R/4R/4R/3R) that is stabilized by the stacking of the 3 beta sheet regions, and by three intermolecular disulfide linkages.

FIG. 24 illustrates examples of two tau peptides that encompass the key structural elements for the tau oligomer dimer that will be used to generate tau oligomer specific monoclonal antibodies. The two peptides were designed to contain all important structural elements leading to dimer formation including the beta-sheet forming regions, cysteines for forming intermolecular disulfide bonds, and the amino acids located between the proline cap regions (Pro270, Pro301, Pro332) that disrupt secondary structure and or provide for a bend in the protein backbone of the parent molecule. Additional peptides may be designed with increased or decreased residues on COO— or amine terminus (plus or minus ten amino acids), or mutations leading to amino acid substitutions found in tauopathies. The beta-sheet forming regions and cysteines are highlighted in bold.

Figure 25:
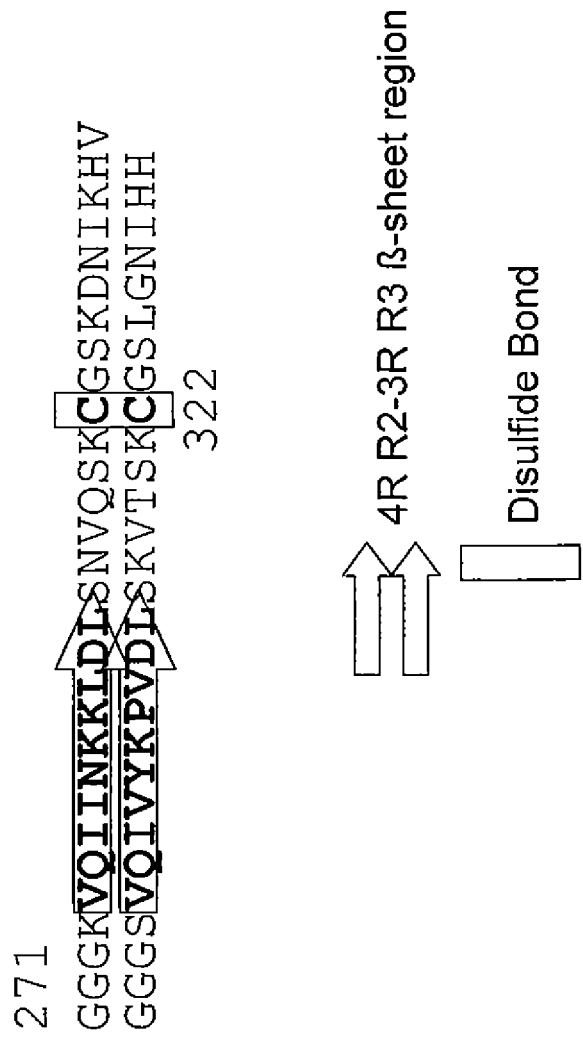

FIG. 25 illustrates a stable tau peptide dimer antigen that will be generated to isolate tau oligomer specific monoclonal antibodies. Tau oligomer specific monoclonal antibodies will be used for drug discovery and diagnostic purposes, but also have utility as potential passive immunotherapeutic agents. The peptide fragments will be adjusted and tested using structural information (i.e. circular dichroism and fourier transform infrared spectroscopy) to select tau peptide dimers with beta-sheet structure. Both R2+R3 and R3+R3 will be used for screening. Tau peptide dimers that are immunologically active, will also be candidates for active immunotherapy.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10 includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "tau protein" includes one, two, three or more tau proteins.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The references, mentioned in the specification, are incorporated herein by reference for all that they disclose.

The headings below are not meant to limit the disclosure in any way; embodiments under any one heading may be used in conjunction with embodiments under any other heading.

In various embodiments, a composition of tau oligomers of 3R and 4R tau is provided, methods for their production are also provided, and their use for the development of therapeutics and biomarkers for Alzheimer's disease and other tauopathies.

The present disclosure includes methods and compositions comprising substantially purified and stabilized tau oligomer or a fragment or a peptide derivative thereof. These tau oligomers and compositions are useful for the identification of biomarkers associated with Alzheimer's disease (AD) or tauopathies. Biomarkers identified according to the methods and compositions disclosed can be used in diagnosing, stratifying, or monitoring the progression or regression of AD or tauopathies. The biomarkers may be used as drug targets to develop new drugs and monitor different medication therapies to treat AD or tauopathies.

Definitions

Tauopathies are a class of neurodegenerative diseases resulting from the pathological aggregation of tau protein in so-called neurofibrillary tangles (NFT) in the brain. Some examples of tauopathies include, but are not limited to, frontotemporal dementia, Alzheimer's disease, progressive supranuclear palsy, corticobasal degeneration, frontotemporal lobar degeneration, also known as Pick's disease, or the like.

"Alzheimer's patient", "AD patient", and all refer to an individual who has been diagnosed with AD (for example, by MMSE score or post mortem by autopsy or has been given a probable diagnosis of Alzheimer's disease (AD). AD includes individuals with a probable diagnosis of mild AD, moderate AD, or severe AD. Non-AD patient refers to a "normal" individual or sample from a "normal" individual who has or would be assessed by a physician as not having AD or mild cognitive impairment (MCI). In various embodiments, a non-AD patient may have a Mini-Mental State Examination (MMSE) (referenced in Folstein et al., J. Psychiatr. Res 1975; 12:1289-198) score or would achieve a MMSE score in the range of 27 or above or assessed by another mental examination method. On average people with Alzheimer's disease who do not receive treatment lose 2 to 4 points each year on the MMSE. An "individual" is a mammal, more preferably a human. Mammals include, but are not limited to, humans, primates, farm animals, sport animals, rodents and pets.

An "individual with mild AD" or "mild AD" is an individual who has been diagnosed with AD (for example, post mortem by autopsy) or has been given a diagnosis of probable AD. In various embodiments, this individual has either been assessed with the Mini-Mental State Examination (MMSE) (referenced in Folstein et al., J. Psychiatr. Res 1975; 12:1289-198) and scored 20-26 or would achieve a score of 20-26 upon MMSE testing or assessed by another mental examination method.

An "individual with moderate AD" or "moderate AD" is an individual who has been diagnosed with AD (for example, post mortem by autopsy) or has been given a diagnosis of probable AD. In various embodiments, this individual has either been assessed with the MMSE and scored 10-19 or would achieve a score of 10-19 upon MMSE testing or assessed by another mental examination method.

An "individual with severe AD" or "severe AD" is an individual who has been diagnosed with AD (for example, post mortem by autopsy) or has been given a diagnosis of probable AD. In various embodiments, this individual has either been assessed with the MMSE and scored below 10 or would achieve a score of below 10 upon MMSE testing or assessed by another mental examination method.

As used herein, methods for "aiding diagnosis" refer to methods that assist in making a clinical determination regarding the presence, or nature, of the AD or MCI or tauopathy, and may or may not be conclusive with respect to the definitive diagnosis. Accordingly, for example, a method of aiding diagnosis of AD or tauopathy can comprise measuring the amount of one or more AD or tauopathy biomarkers in a biological sample from an individual.

The term "stratifying" refers to sorting individuals into different classes or strata based on the features of AD or tauopathy. For example, stratifying a population of individuals with Alzheimer's disease involves assigning the individuals on the basis of the severity of the disease (e.g., mild, moderate, severe, etc.).

As used herein, the term "treatment" refers to the alleviation, amelioration, and/or stabilization of symptoms, as well as delay in progression of symptoms of a particular disorder. For example, "treatment" of AD includes any one or more of: elimination of one or more symptoms of AD, reduction of one or more symptoms of AD, stabilization of the symptoms of AD (e.g., failure to progress to more advanced stages of AD), and delay in progression (e.g., worsening) of one or more symptoms of AD, and regression (e.g., reverting back to the earlier stage of AD).

As used herein, the term "predicting" refers to making a finding that an individual has a significantly enhanced probability of developing AD or tauopathy. The term "prognosis" includes the likely outcome or course of AD or tauopathy.

In various embodiments of the present application, we disclose novel purified and stabilized tau oligomer or a fragment or a peptide derivative thereof. Tau protein exists in 6 isoforms of 352-441 amino acid residues in the adult brain. The term "tau protein" refers to any protein of the tau protein family including, but not limited to, native tau protein monomer, precursor tau proteins, tau peptides, tau intermediates, metabolites, tau derivatives that can be antigenic, or antigenic or non-antigenic fragments thereof.

Fragments include less than entire tau protein provided the fragment is antigenic and will cause antibodies or antibody binding fragments to react with the tau fragment. Non-reactive tau oligomer can be one composed of 3R tau (i.e. 3r/3R tau dimer or 3R/4R/3R tau trimer), or one in which further oxidation has rendered the sulfonic derivative, or one where truncation has occurred removing the cysteine thiol.

The tau protein family in addition is characterized by the presence of a characteristic N-terminal segment which is shared by all members of the family, sequences of approximately 50 amino acids inserted in the N-terminal segment, which are developmentally regulated in the brain, a characteristic tandem repeat region consisting of 3 or 4 tandem repeats of 31-32 amino acids, and a C-terminal tail. In various embodiments, tau protein has the following amino acid sequence shown SEQ ID NOS. 1-6. Embodiments of tau protein may have an amino acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical or substantially identical to the sequence given in SEQ ID NOS: 1-6.

As applied to any of the disclosed tau protein, peptides, the term "substantially identical" means that two peptide or protein sequences, when optimally aligned, such as by the programs GAP or BESTFIT using default gap weights, share at least 70 percent sequence identity, such as at least 90 percent sequence identity, or at least 95 percent sequence identity, or at least 99 percent sequence identity. Residue positions, which are not identical, in various embodiments, differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. In various embodiments, conservative amino acids substitution groups are: valine-leucine-isoleucine, phenylalanine-tyrosine, lysine-arginine, alanine-valine, glutamic-aspartic, and asparagine-glutamine.

In various embodiments, tau monomeric units (tau proteins (e.g., SEQ ID NOS: 1-6), peptides, or fragments thereof) may oligomerize and form tau oligomers, which are soluble in bodily fluids (e.g., CSF, blood, urine, cytoplasmic fluid, etc.). It has been found by Applicants that extracellular soluble tau monomeric units and/or tau oligomers increase in AD or tauopathies.

Tau oligomerization includes multimerizing two or more tau proteins, tau peptides, tau intermediates, tau metabolites, tau derivatives that can be antigenic, tau antigenic fragments, or tau-tau complexes. The multimer can contain any desired number of tau peptide/protein complexes and thus can form any multimer, such as but not limited to, a dimer, a trimer, a tetramer, a pentamer, a hexamer, octamer, decamer, dodecamer, or the like. However, in order to be soluble in bodily fluids (e.g., CSF, blood, urine, etc.) the multimer cannot be too long as it may become insoluble in bodily fluids. By "insoluble" is meant that the tau oligomer will precipitate out of the bodily fluid. In various embodiments, tau oligomer that comprises 50 tau monomer units is too long and may be insoluble in bodily fluids. In other embodiments, tau oligomer that comprises 100 tau monomer units is too long and may be insoluble in bodily fluids. By "soluble" is meant that the tau oligomer will dissolve in the bodily fluid. For example, soluble tau may be extracellular and appear in the CSF. By associated is meant covalent or non-covalent, hydrophobic or hydrophilic interactions, H bonding, or van der Waals attachment.

Tau proteins, peptides, or fragments thereof may undergo truncation at one or more sites (e.g., carboxy and/or amino truncations). For example, tau proteins may have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acid truncation at the N and/or C terminus. Truncation typically occurs by enzymes, which cleave at the carboxy or amino terminus. Such enzymes, include, but are not limited to caspases that comprise cysteine proteases.

Figure 1:
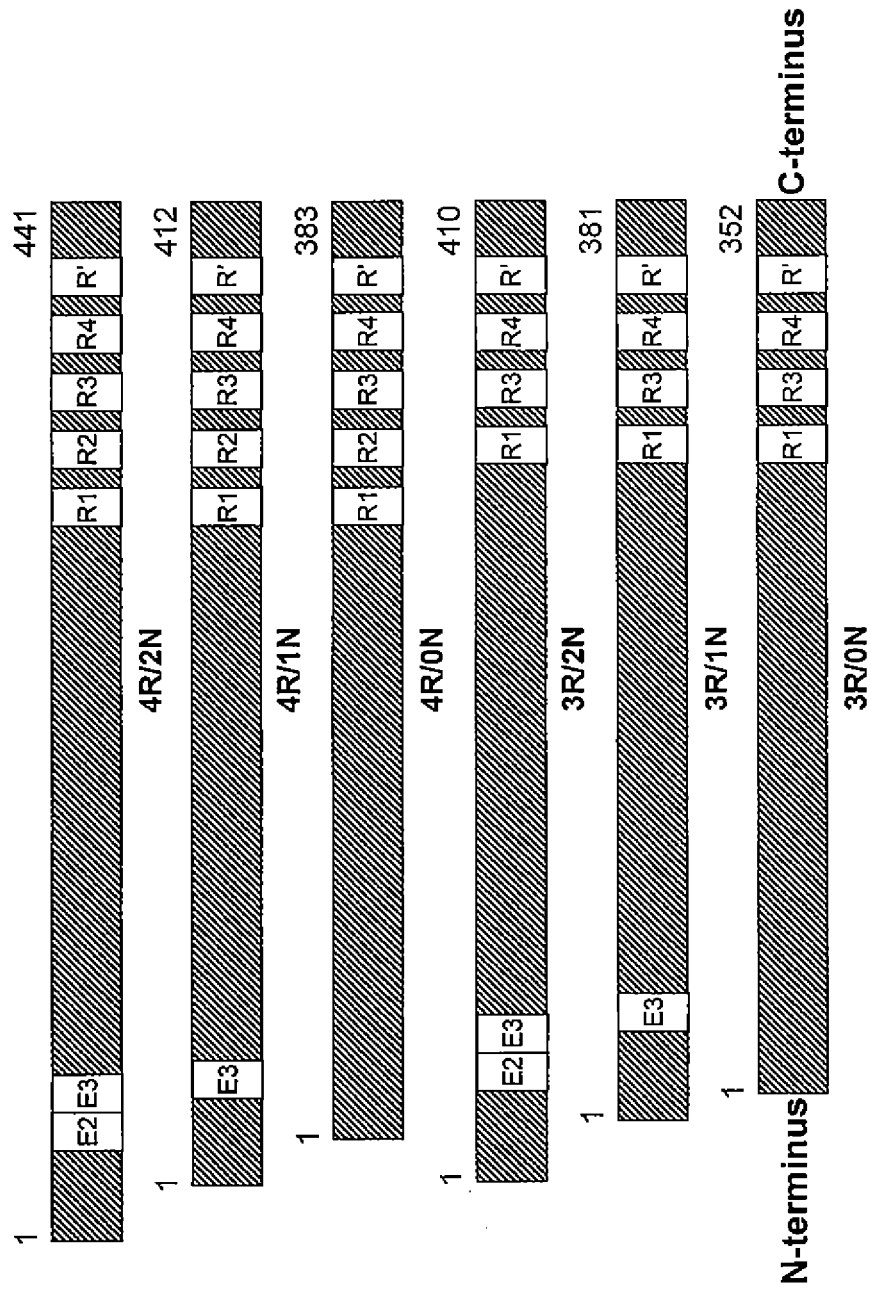
FIG. 1 illustrates the six tau protein isoforms that result from alternate splicing with the N-terminal inserts in the acidic domain (E2 and E3), the repeat domains of the microtubule binding region (R1, R2, R3 and R4) and the tau pseudo repeat (R') indicated. Note that there are three tau protein isoforms with three repeats (tau352, tau381 and tau410 only contain repeats R1, R3 and R4) and three tau protein isoforms with four repeats (tau383, tau412 and tau441) in the microtubule binding domain (R1, R2, R3 and R4).
Figure 2:
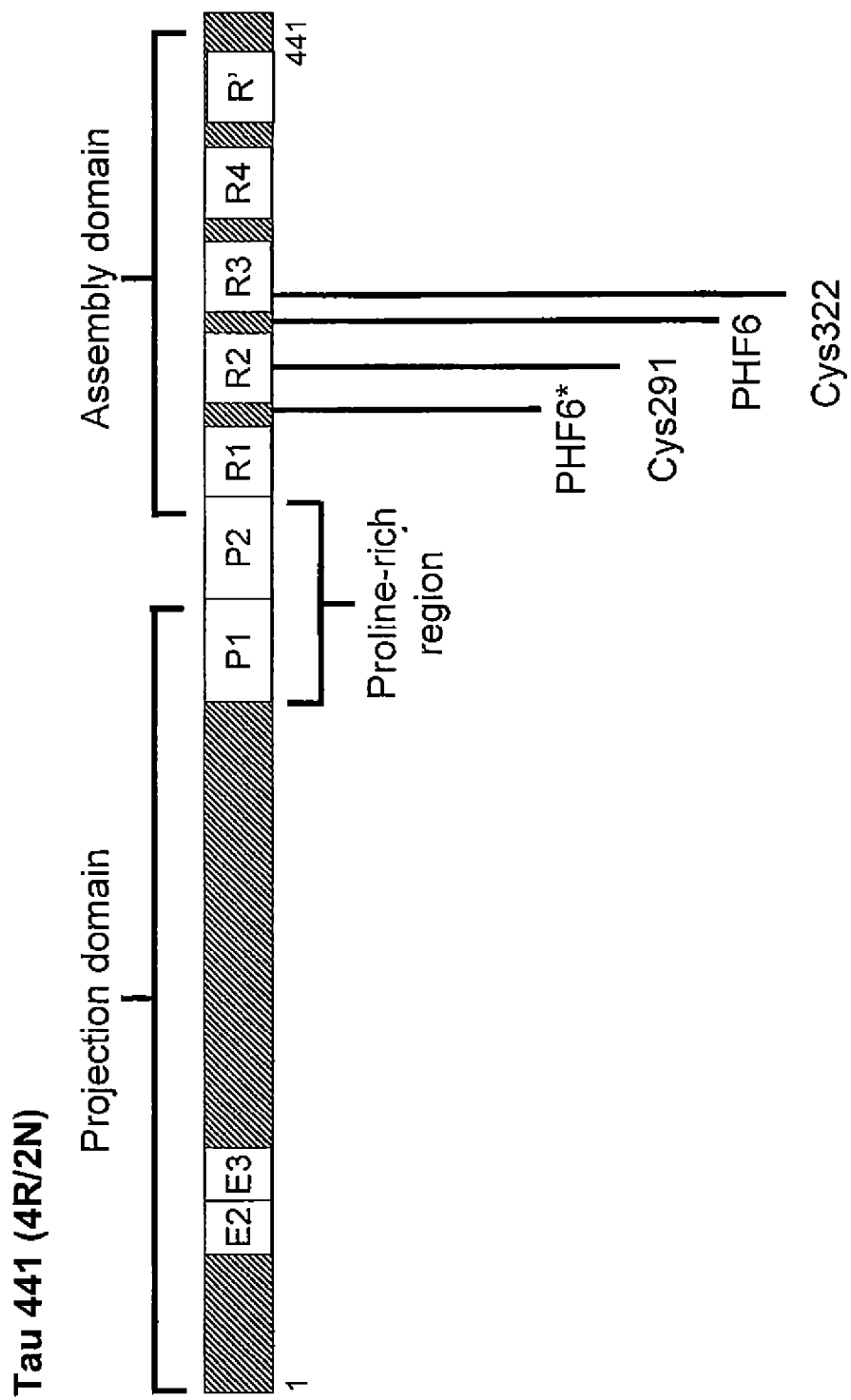
FIG. 2 illustrates tau441 structural features including the projection domain (N-terminal), the proline rich region, and assembly domain (C-terminal). Also indicated is the beta-sheet forming regions (PHF6* and PHF6) and the two cysteines (Cys291 in R2 and Cys322 in R3). All 4R tau protein isoforms contain four repeat regions as shown (R1, R2, R3 and R4), whereas 3R tau protein isoforms only contain three repeat regions (R1, R3 and R4).
Figure 3:
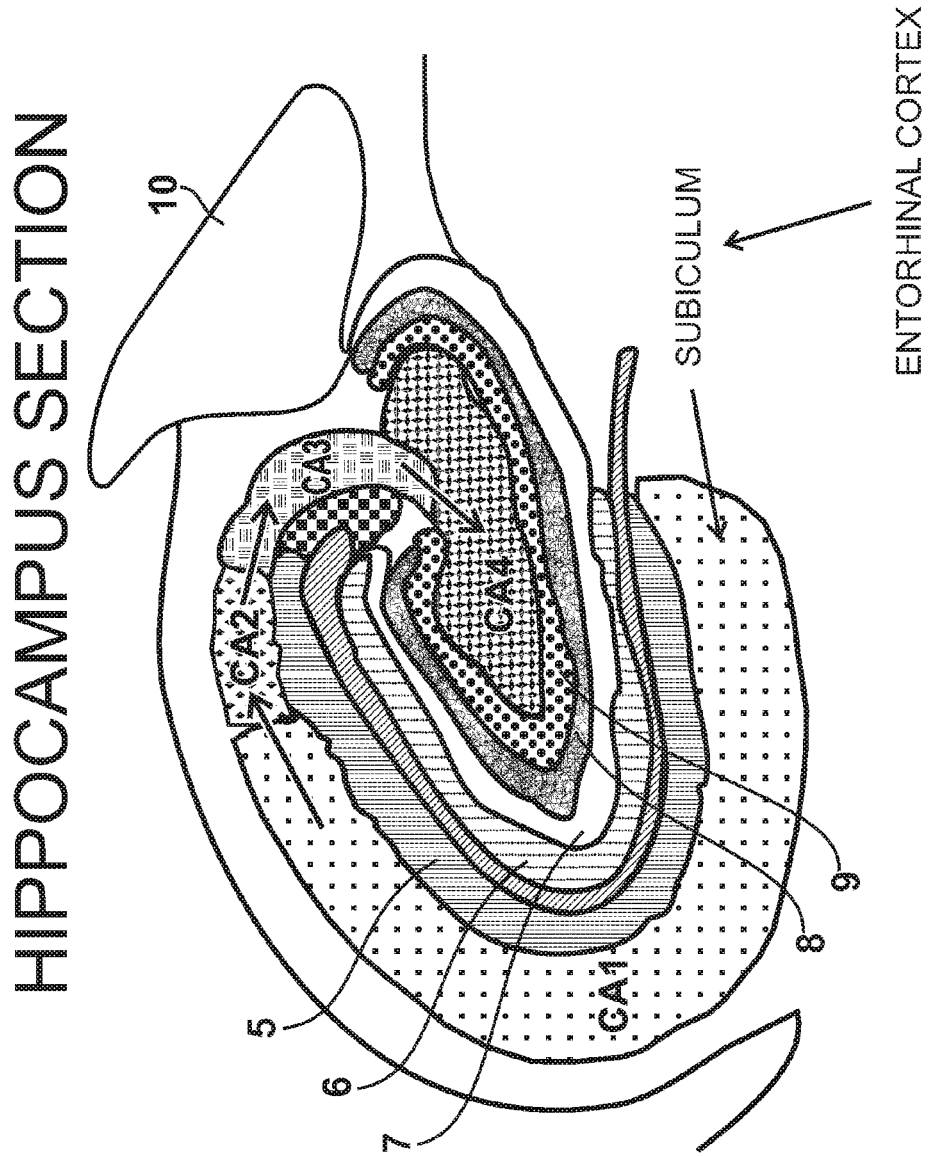
FIG. 3 illustrates the contiguous spread of tau pathology is a hallmark of AD. As AD progresses, tau pathology engulfs the hippocampal structure in a highly selective and orderly fashion.
Figure 4:
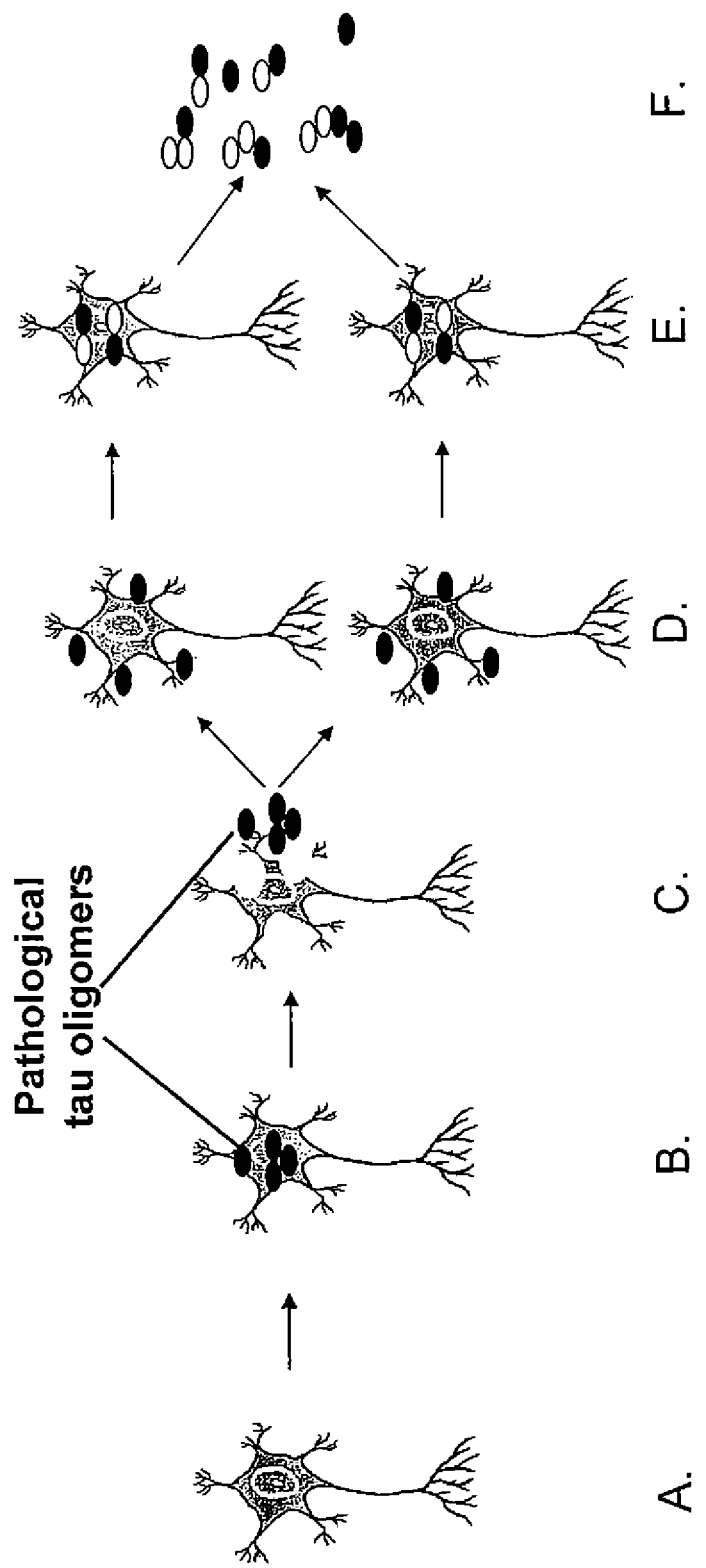
FIG. 4 illustrates the proposed mechanism of tau oligomer-mediated disease propagation. An upstream event such as oxidation, physical damage, chemical damage, infection and/or effects mediated by upstream Aβ induced pathology (A.); leads to accumulation of tau off of microtubules and intracellular tau oligomer formation (tau dimer, tau trimer, etc.) (B.); cell death results in release of tau oligomers extracellularly (C.); whereby extracellular tau oligomers bind to healthy neurons (D.); leading to the uptake of tau oligomers into healthy cells, and the subsequent promotion of the formation of additional tau oligomers and a diseased cell phenotype (E.); The rate of propagation is directly proportional to the level of extracellular tau oligomer (F.).
Figure 5:
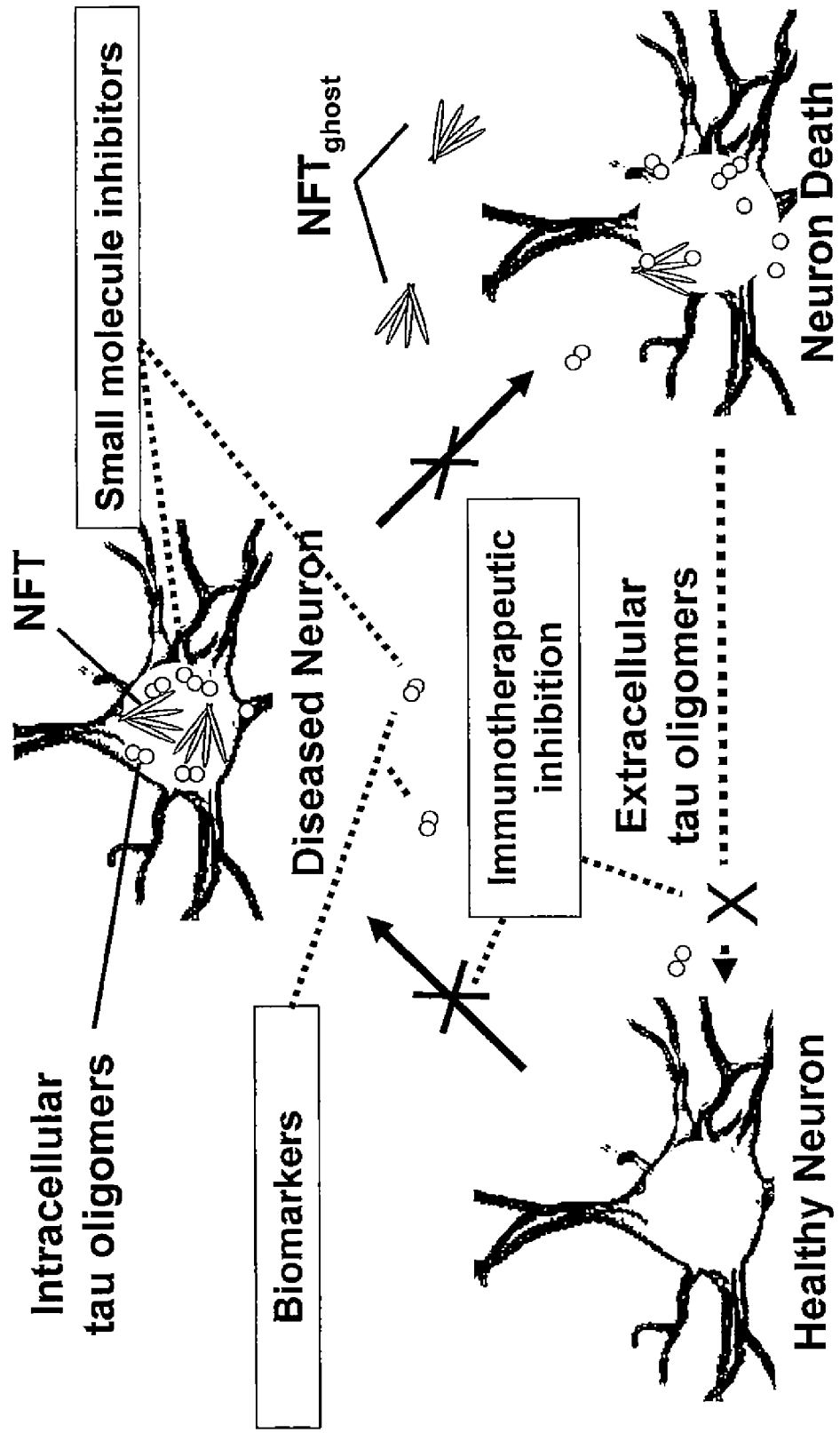
FIG. 5 illustrates the therapeutic intervention points for halting or arresting disease progression based on small molecule drugs for intracellular and extracellular tau oligomers (arrest disease process within a neuron and arrest spread of tau pathology to neighboring healthy cells), and for active or passive immunotherapy targeting extracellular tau oligomers (arrest spread of tau pathology to neighboring healthy cells). The extracellular tau oligomers are useful biomarkers for disease progression.

In some embodiments, the tau protein has six isoforms. The six tau isoforms expressed by alternated splicing of the primary transcript of the MAPT gene on chromosome 17q21. The six tau isoforms expressed in the central nervous system (see FIG. 1); SEQ ID NO. 1-6. The convention used for amino acid numbering is based on the longest of the six tau isoforms containing 441 amino acids. R1 includes the first microtubule-binding repeat. R2 includes the second microtubule-binding repeat. R3 includes the third microtubule-binding repeat. R4 includes the fourth microtubule-binding repeat. R' includes the pseudo microtubule-binding repeat.

3R tau: includes tau isoforms 3R/0N, 3R/1N, 3R/2N, containing 410, 381 or 352 amino acids, lacking the second microtubule-binding repeat (R2) due to alternate splicing of exon 10, and containing 0, 1 or 2 N-terminal inserts due to alternate splicing of exons 2 or 3 (FIG. 1). 3R tau also includes fragments or peptides of tau including the 3R microtubule binding domain.

4R tau: includes tau isoforms 4R/0N, 4R/1N, 4R/2N containing 441, 412 or 383 amino acids containing all microtubule-binding repeats including R2, and containing 0, 1 or 2 N-terminal inserts due to alternate splicing of exons 2 or 3 (FIG. 1). 4R tau also includes fragments or peptides of tau including the 4R microtubule binding domain.

PHF6* includes a hexapeptide motif 275vqiink280 (residues 275-280 of SEQ ID NO: 6) and exhibits propensity to form bet-sheet structure.

PHF6 includes the hexapeptide motif 306vqivyk311 (residues 306-311 of SEQ ID NO: 6) and exhibits propensity to form bet-sheet structure.

Tau monomer includes any individual 3R or 4R tau.

Tau oligomer includes an aggregate of tau protein subunits. The minimal size of a tau oligomer is two subunits, and the maximal size of a tau oligomer referred to in this application is 12 tau subunits. These tau oligomers are tau dimer, tau trimer, tau tetramer, tau pentamer, tau hexamer, tau septamer, tau octamer, tau nonamer, tau decamer, tau unadecamer, tau dodecamer. The tau oligomer subunits may be composed of any 3R or 4R tau. In some embodiments, the tau oligomer may be substantially purified and/or isolated. Tau protein may be purified by cation exchange using SP Sepharose, heat denaturation in Laemmli sample buffer 5 min at 95° C., and fraction collection from continuous SDS PAGE gel electrophoresis. Tau oligomers may be formed by incubation of tau subunits in buffer (50 mM Tris pH 7.4) at 37° C. The size range of the oligomers may be controlled by modulation of tau concentration, length of incubation, buffer composition, and/or choice of tau isoforms, fragment or peptide and/or mixtures thereof. In some embodiments, the tau oligomer subunits may or may not be linked by disulfide bonds.

In some embodiments, the tau subunits interact in a specific orientation such that: during 3R tau-3R tau intermolecular association the hexapeptide motif PHF6 in R3 of one 3R subunit aligns with the hexapeptide motif PHF6 in R3 the other 3R tau subunit in the same amino to carboxyl orientation such that they may form cross beta strand structure; such that cysteine322 in R3 in one 3R tau subunit and cysteine322 in R3 in the other 3R tau subunit are aligned enabling disulfide bond formation; such that there are no free thiol groups and hexapeptide motifs in each of the 3R tau subunits precluding similar associations with additional 4R or 3R tau subunits (FIG. 18). During 4R tau-4R tau intermolecular association the hexapeptide motif PHF6* in R2 of one tau subunit aligns with the hexapeptide motif PHF6 in R3 of the other 4R tau subunit in the same amino to carboxyl orientation such that they may form cross beta strand structure; such that cysteine291 in R2 and cysteine322 in R3 are aligned enabling disulfide bond formation; such that there are a free thiol group and hexapeptide motif in each of the 4R tau subunits enabling similar associations with additional 4R or 3R tau subunits facilitating oligomer extension from either end (FIG. 21). During 4R tau-3R tau intermolecular association the hexapeptide motif PHF6* in R2 of the 4R tau subunit aligns with the hexapeptide motif PHF6 in R3 of the 3R tau subunit in the same amino to carboxyl orientation such that they may form cross beta strand structure; such that cysteine291 in R2 of 4R tau and cysteine322 in R3 of 3R tau are aligned enabling disulfide bond formation; such that there is unidirectional oligomer extension from the 4R tau end of the oligomer containing one free thiol group and one hexapeptide motif and termination of oligomer extension from the 3R end with no free hexapeptide motifs or thiols (see FIG. 22); such that addition of 3R tau to both end of an oligomer terminates oligomer extension through this mechanism (FIG. 23). The cross beta sheet structures in the oligomer may stack in antiparallel orientation (FIG. 24). Oligomer size may be controlled by modulation of the ratio of 3R to 4R tau concentrations (FIG. 19).

In some embodiments, a tau dimer target is provided. The composition of a dimer composed of R2 and R3 peptides such as 271GGGKVQIINKKLDLSNVQSKCGSKD-NIKHV300(residues 271-300 of SEQ ID NO: 6), and 302GGGSVQIVYKPVDLSKVTSKCGSLGNIHH330 (residues 302-330 of SEQ ID NO: 6) that are designed to contain all important structural elements leading to dimer formation including β-sheet forming regions PHF6* and PHF6, cysteines for forming intermolecular disulfide bonds, and the amino acids located between the proline cap regions (Pro270, Pro301, Pro332) that disrupt secondary structure. Additional peptides may be designed with increased or decreased residues on COO— or amine terminus, or mutations found in tauopathies (FIG. 25).

An "isolated" tau oligomer or tau peptide derivative, or tau fragment, as used herein, means a naturally-occurring tau oligomer or peptide or fragment that has been separated or substantially separated from the cellular components (e.g., CSF, brain cells, other peptides, etc.) that naturally accompany it by purification, recombinant synthesis, or chemical synthesis, and also encompasses non-naturally-occurring recombinantly or chemically synthesized oligomers or peptides or fragments that have been purified or substantially purified from cellular components, biological materials, chemical precursors, or other chemicals. In vitro methods of making tau oligomer are described in U.S. application Ser. No. 11/704,079, filed Feb. 8, 2007 and U.S. Publication No. 20070218491, which is hereby incorporated by reference into the present disclosure.

"Purified" as used herein includes that the protein, peptide derivative or fragment thereof is free not only of other proteins, but also of other materials used in the isolation and identification of the protein, such as, for example, sodium dodecyl sulfate and other detergents as well as the support material. The protein is at least 90% free, preferably at least 95% free and, more preferably, at least 98% or 99% free of such materials.

"Stabilized" tau oligomer or tau peptide derivative, or tau fragment is a form of tau oligomer characterized by an increase in $T_m$ over tau monomer. In some examples the tau oligomer is stabilized by two or more disulfide bonds. In some embodiments, the tau oligomer is stabilized by disulfide bonds is stable for at least two months in a non-reductive environment.

In some embodiments, the aggregates are stable under stringent denaturing conditions and high temperature and detergent. They can also be stable for months to years. Reducing conditions such as with reducing buffer conditions will make the tau aggregates unstable. Less than the full length Tau oligomer can be a peptide. "Peptide" comprises a string of at least three amino acids linked together by peptide bonds. Peptide may refer to an individual peptide or a collection of peptides. Inventive peptides may contain only natural amino acids, although non-natural amino acids (i.e., compounds that do not occur in nature but that can be incorporated into a polypeptide chain; see, for example, www.cco.caltech.edu/.about.dadgrp/Unnatstruct.gif, which displays structures of non-natural amino acids that have been successfully incorporated into functional ion channels) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. These modifications may include cyclization of the peptide, the incorporation of D-amino acids, etc. None of the modifications should substantially interfere with the desired biological activity of the peptide.

"Peptide derivatives" includes derivatives (chemically functionalized protein molecules obtained starting with the disclosed protein sequences) or mimetics (three-dimensionally similar chemicals) of the native tau oligomer, as well as proteins sequence variants (such as mutants), genetic alleles, fusions proteins of tau or combinations thereof.

A "free thiol moiety" refers to the amino acid (e.g., cysteine) which has a thiol functional group (—SH), and is not paired as an intramolecular or intermolecular disulfide bridge.

"Tau-Aβ complex" includes interactions, aggregates, and/or coupling between tau, tau intermediates, metabolites, tau derivatives, or antigenic fragments of tau and β-amyloid protein (Aβ1-42), Aβ1-42 intermediates, Aβ1-42 metabolites, Aβ1-42 derivatives, or antigenic fragments of Aβ1-42. Aβ1-42 comprises 42 amino acids (SEQ ID NO: 7). In various embodiments, tau-Aβ complex comprises at least tau and β-amyloid protein (Aβ1-42) or tau and Aβ1-40 protein. In various embodiments, tau-Aβ complex comprises at least tau and β-amyloid protein (Aβ1-42) or tau and Aβ1-40 protein and tau and Aβ1-42 or Aβ1-40 molecules, such as, for example, amyloid oligomer, other amyloid protein, tau-oligomer-Aβ1-42 or tau and Aβ1-40 protein.

"Amyloid" refers to amyloidogenic proteins, peptides, or fragments thereof which can be soluble (e.g., monomeric or oligomeric) see, e.g., Lambert et al., Proc. Natl. Acad. Sci. U.S.A. 95, 6448-6453 (1998)). β-amyloid protein (Aβ) may comprise 39-43 amino acids. Typically, the Aβ1-42 peptide is produced by sequential proteolytic cleavage of the amyloid precursor protein (APP) by the enzyme(s) beta and gamma secretases. The length of the Aβ peptide appears to dramatically alter its biochemical/biophysical properties. Specifically, the additional two amino acids at the C-terminus of Aβ1-42 are very hydrophobic, presumably increasing the propensity of Aβ1-42 to aggregate. For example, Jarrett et al. demonstrated that Aβ1-42 aggregates vary rapidly in vitro as compared to Aβ1-40, suggesting that the longer forms of Aβ may be the important pathological proteins that are involved in the initial seeding of the neuritic plaques in Alzheimer's disease (Jarrett et al., Biochemistry 32, 4693-4697 (1993); Jarrett et al., Ann. NY Acad. Sci. 695, 144-148, (1993)).

As used herein, the term "β-amyloid" or "Aβ" or "amyloid beta" refer to amyloid beta proteins or peptides, amyloid beta precursor proteins or peptides, intermediates, and modifications and immunologic fragments thereof, unless otherwise specifically indicated. In particular, "Aβ" refers to any peptide produced by proteolytic processing of the APP gene product or peptides that are associated with amyloid pathologies, including Aβ1-39, Aβ1-40, Aβ1-41, Aβ1-42, and Aβ1-43. Embodiments of Aβ1-42 may have an amino acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical or substantially identical to the sequence given in SEQ ID NO: 7.

In some embodiments, the aggregation core, contains all of the important structural elements for the dimer binding interface between the two monomers and will be used to isolate tau oligomer specific antibodies that recognize this structural epitope.

The purified and stabilized tau oligomer or a fragment or a peptide derivative thereof can be used as a biomarker. A "biomarker" includes, protein(s), peptide(s), protein-protein complexes or aggregates, protein-peptide complexes or aggregates, peptide-peptide complexes or aggregates, immunogenic fragments, or metabolite(s) (e.g., glycated, truncated, phosphorylated peptide, protein, complex, aggregates) whose presence, absence, or, level of expression is a measure of the progression or regression of tauopathy, AD or of the likelihood of developing tauopathy, or AD. A biomarker may comprise a single protein, peptide, protein-protein complex, protein-peptide complex, peptide-peptide complex or metabolite, or it may comprise a plurality of proteins, peptides, complexes, immunogenic fragments and/or metabolites whose presence, absence, or levels of expression collectively provide a measure of the progression or regression of tauopathy, AD or of the likelihood of developing a tauopathy or AD.

The purified and stabilized tau oligomer or a fragment or a peptide derivative thereof can be used as an epitope or antigen to generate antibodies thereto. The term "epitope" or "antigenic determinant" refers to a site on an antigen to which B and/or T cells respond or a site on a molecule against which an antibody will be produced and/or to which an antibody will bind. For example, an epitope can be recognized by an antibody defining the epitope. A "linear epitope" is an epitope where an amino acid primary sequence comprises the epitope recognized. A linear epitope typically includes at least 3, and more usually, at least 5, for example, about 8 to about 10 amino acids in a unique sequence. A "conformational epitope", in contrast to a linear epitope, is an epitope wherein the primary sequence of the amino acids comprising the epitope is not the sole defining component of the epitope recognized (e.g., an epitope wherein the primary sequence of amino acids is not necessarily recognized by the antibody defining the epitope). Typically a conformational epitope comprises an increased number of amino acids relative to a linear epitope. With regard to recognition of conformational epitopes, the antibody recognizes a 3-dimensional structure of the peptide or protein or fragment thereof. For example, when a protein molecule folds to form a three dimensional structure, certain amino acids and/or the polypeptide backbone forming the conformational epitope become juxtaposed enabling the antibody to recognize the epitope. Methods of determining conformation of epitopes include but are not limited to, for example, x-ray crystallography 2-dimensional nuclear magnetic resonance spectroscopy and site-directed spin labeling and electron paramagnetic resonance spectroscopy.

The term "antibody" is used to include intact antibodies and binding fragments thereof, including but not limited to, for example, full-length antibodies (e.g., an IgG antibody) or only an antigen binding portion (e.g., a Fab, F(ab')$_2$ or scFv fragment). The fragment can also be generated by phage display technology known in the art.

Typically, fragments compete with the intact antibody from which they were derived for specific binding to an antigen. Optionally, antibodies or binding fragments thereof, can be chemically conjugated to, or expressed as, fusion proteins with other proteins. The term "antibody fragment" refers to a portion of a full-length antibody, generally the antigen binding or variable region. Examples of antibody fragments include Fab, Fab', F(ab')$_2$ and Fv fragments. In various embodiments, papain digestion of antibodies produces two identical antigen binding fragments, called the Fab fragment, each with a single antigen binding site, and a residual "Fc" fragment, so-called for its ability to crystallize readily. In various embodiments, pepsin treatment yields an F(ab')$_2$ fragment that has two antigen binding fragments which are capable of cross-linking antigen, and a residual other fragment (which is termed pFc'). As used herein, "functional fragment" with respect to antibodies, refers to Fv, F(ab) and F(ab')$_2$ fragments.

An "Fv" fragment is the minimum antibody fragment, which contains a complete antigen recognition and binding site. This region consists of a dimer of one heavy and one light chain variable domain in a tight, non-covalent association ($V_H$-$V_L$ dimer). It is in this configuration that the three complementarity determining regions (CDRs) of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site. The Fab fragment (also designated as F(ab)) also contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. Fab'-SH is the designation herein for Fab' in which the cysteine residue(s) of the constant domains have a free thiol group. F(ab') fragments are produced by cleavage of the disulfide bond at the hinge-cysteines of the F(ab')$_2$ pepsin digestion product. Additional chemical couplings of antibody fragments are known to those of ordinary skill in the art.

The term "monoclonal antibody" as used herein refers to an antibody obtained from a population of substantially homogeneous antibodies, e.g., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations, which typically include different antibodies, directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature 256, 495 (1975), or may be made by recombinant methods, e.g., as described in U.S. Pat. No. 4,816,567. "Polyclonal antibodies" include different antibodies directed against different determinants (epitopes).

"Specific binding" or "binding specifically" between two entities, may include a binding affinity of at least $10^6$, $10^7$, $10^8$, $10^9 M^{-1}$, or $10^{10} M^{-1}$. Affinities greater than $10^8 M^{-1}$ are preferred for specific binding. Antibodies to tau are described in U.S. patent application Ser. No. 12/069,399, filed Feb. 8, 2008 and published as US-2008-0220449. The entire disclosure is hereby incorporated by reference into the present disclosure.

The tau oligomer or a fragment or a peptide derivative thereof can be used as an immunotherapeutic agent. The term "immunotherapeutic agent" is intended to mean an agent that stimulates anti-tau oligomer immunity. Agents that stimulate anti-tau oligomer activity are preferably those that directly or indirectly stimulate T-cells and/or NK cells to stop the oligomerization of tau to achieve a prophylactic and/or therapeutic goal. The tau oligomer or a fragment or a peptide derivative thereof can be used to make antibodies for passive immunotherapies or the tau oligomer or a fragment or a peptide derivative thereof can be used for active immunity, such as for example, in a vaccine composition when administered to the mammal.

The tau oligomer or a fragment or a peptide derivative thereof can be used with adjuvants and administered to the animal. Any adjuvant may be used in accordance with the present invention. A large number of adjuvant compounds is known; a useful compendium of many such compounds is prepared by the National Institutes of Health and can be found on the world wide web (www.niaid.nih.gov/daids/vaccine/pdf/compendium.pdf, incorporated herein by reference; see also Allison Dev. Biol. Stand. 92:3-11, 1998; Unkeless et al. Annu. Rev. Immunol. 6:251-281, 1998; and Phillips et al. Vaccine 10:151-158, 1992, each of which is incorporated herein by reference). Hundreds of different adjuvants are known in the art and could be employed in the practice of the present invention.

The tau oligomer or a fragment or a peptide derivative thereof can be administered to the animal in a pharmaceutical composition. Those of ordinary skill in the art will appreciate that pharmaceutical composition can be administered to individuals via any of a variety of routes, protocols, and dosing regimens. Known routes of administration include, for example, intravenous (IV), intraperitoneal (IP), intragastric (IG), subcutaneous (SQ), intramuscular (IM), oral (PO), rectal (PR), intrathecal, vaginal, intranasal, transdermal, intradermal, subcutaneous, intrathecal, epidural, or the like.

The tau oligomer or a fragment or a peptide derivative thereof can be part of a pharmaceutical composition designed for administration to the mammal. Pharmaceutical compositions for use in accordance with the present application may include a pharmaceutically acceptable excipient or carrier. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and/or to animals, orally, rectally, parenterally, intracisternally, intravaginally, intranasally, intraperitoneally, topically (as by powders, creams, ointments, or drops), bucally, or as an oral or nasal spray.

Any dose can be administered to an animal. Dosages can vary depending on the relative potency of individual compositions, and can generally be estimated based on data obtained from in vitro and in vivo animal models. Typically, the dosage may be from about 0.01 micrograms to about 100 g per kg of body weight, and may be given once or more daily, weekly, or even less often. Following successful administration, it may be desirable to have the subject undergo additional booster administrations to maintain a suitable level of the anti-tau oligomer, tau fragment, or tau-peptide activity. For example, an additional dosage can be administered 6, 12, 24, 36, 48, 60 or more months after an initial dosage. In some cases, additional dosages can be administered every 6, 12, 18, 24, 30, 36, 42, 48, 54, 60 or more months after an initial dosage. Additional dosages also can be administered as needed.

The term "animal", as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). An animal may be a transgenic animal.

The tau oligomer or a fragment or a peptide derivative thereof can be used a drug target in drug discovery. In various embodiments, methods of screening for candidate agents for the treatment of AD or tauopathies are provided by assaying prospective candidate agents for activity in modulating tau oligomer or a fragment or a peptide derivative of tau oligomer. The screening methods may utilize tau oligomer or a fragment or a peptide derivative of tau oligomer described herein as "drug targets." Prospective agents are tested for activity in modulating a drug target in an assay system. As will be understood by those of skill in the art, the mode of testing for modulation activity will depend on the biomarker and the form of the drug target used (e.g., complete protein or peptide fragment).

When the tau oligomer or a fragment or a peptide derivative of tau oligomer itself is the drug target, prospective agents are tested for activity in modulating levels or activity of the protein/peptide itself (e.g., soluble tau oligomer). Modulation of levels of tau oligomer or a fragment or a peptide derivative of tau oligomer can be accomplished by, for example, increasing or reducing half-life of the biomarker protein or drug candidate concentration. Modulation of activity of tau oligomer or a fragment or a peptide derivative of tau oligomer can also be accomplished by increasing or reducing the availability of the tau oligomer or a fragment or a peptide derivative of tau oligomer to bind to its receptor(s) or ligand(s). In various embodiments, a method of screening an agent for modulation or disruption of tau oligomer or a fragment or a peptide derivative of tau oligomer is provided, the method comprising: a) contacting a sample containing tau oligomer or a fragment or a peptide derivative of tau oligomer with an agent suspected of being capable of modulating tau oligomer formation or disrupting tau oligomers; and b) detecting the amount of tau oligomer or a fragment or a peptide derivative of tau oligomer in the sample, wherein a decrease in soluble tau oligomer indicates that the agent modulates tau oligomer formation or disrupts tau oligomer. In various embodiments, the mechanism that the agent disrupts tau oligomer formation is by inhibiting tau-tau binding.

The screening assay can also be used to determine effective doses of agents to optimize disruption or modulation of tau oligomer. For example, the method of screening compounds may involve comparing the sample being analyzed to a sample that does not contain the agent or less agent to determine if the agent modulates or inhibits tau oligomer. "Disruption" of tau oligomer includes the interruption of tau oligomer formation.

Prospective agents for use in the screening methods may be chemical compounds and/or complexes of any sort, including both organic and inorganic molecules (and complexes thereof). As will be understood in the art, organic molecules are most commonly screened for AD biomarker modulatory activity. In some situations, the prospective agents for testing will include the target AD biomarker (e.g., soluble tau oligomer). Suitable agents for screening include, but are not limited to, antioxidants (vitamin E and vitamin C), anti-inflammatory agents (e.g., curcumin, demethoxycurcumin, bis-demethoxycurcumin, and/or morin), antibiotics, chelation agents, cliouinol, ergoloids, estrogen, herbal agents (e.g., ginko biloba, huperzine A, melissa officinalis (lemon balm), etc.), statins, vitamin B, or combinations thereof or derivatives thereof. Derivatives include analogs of the above agents that are pharmacologically active.

We have found that the alignment of tau subunits is staggered such that in oligomers composed of 4R tau or 4R and 3R tau the R2 of 4R tau interacts with the R3 of the associating 4R or 3R tau, whereas in other models the repeat units are fully aligned. This model describes the formation of pure or mixed 3R and 4R tau oligomers, whereas other models describe oligomerization of 3R or 4R tau individually. This model provides the composition of nucleating structures for tau oligomerization and a mechanism for their extension and termination of extension, whereas other mechanisms have no mechanism for terminating extension. This patent application discloses composition and methods for producing and purifying tau oligomers of different sizes and compositions by modulating the relative concentration of 3R and 4R tau. This model provides a depiction of how cross beta sheet structures in disulfide-linked tau oligomers can stack in antiparallel orientation due to their staggered association (FIG. 24). This model explains the toxicity of the relative overexpression of 4R to 3R tau in multiple neurodegenerative diseases because higher 4R tau levels favors nucleation of extension competent dimers and their extension. The methods described here enable the purification of tau oligomer structures for the development of therapeutics and biomarkers. This model provides the composition of tau oligomer structures that can be used for the development of passive or active immunotherapeutics. The composition and methods provided here enable the development of antibodies for biomarkers for Alzheimer's disease and other tauopathies. This model provides unique targets for small molecule drug discovery for inhibiting the formation of tau oligomers. The novel dimer target enables the development of disease-modifying immunotherapeutics that cause the reduction of extracellular tau oligomers involved in transmission of tau pathology to neighboring neurons. The novel dimer target enables the development of disease-modifying small molecule drugs modulating intracellular and extracellular tau oligomer formation. The novel dimer target enables the development of antibodies for the development of biomarkers for Alzheimer's disease and other tauopathies.

Tau Protein Structure and Function

Tau is encoded by the MAPT gene located on the long (q) arm of chromosome 17 at position 21.1. Alternative splicing of the second and third exons in the N-terminal portion of tau and the tenth exon yields a total of six protein isoforms. Tau is an intrinsically unstructured protein due to its very low hydrophobic content and has been characterized to have a projection domain, a basic proline-rich region, and an assembly domain. The domain in the carboxyl-terminal portion of the protein critical for tau self-association into oligomers and fibrils, the assembly domain, contains either three or four repeats (3R or 4R) of a conserved tubulin-binding motif depending on alternative splicing of exon 10 encoding the second repeat (Lee et al. 1989). Hexapeptide motifs PHF6* and PHF6 in the second and third repeats, respectively, have propensity to form β-sheet structures which are involved in tau interaction with tubulin to form MTs and tau self-interaction to form pathological aggregates such as paired helical filaments (PHF) (von Bergen et al.

2000; Amos 2004). Tau 4R isoforms have greater microtubule stabilizing ability than 3R isoforms. Only the shortest 3R tau isoform is expressed during fetal development where there are dynamic changes in the cytoskeleton, whereas adult brain normally has a ratio of about 1:1 for 3R to 4R isoforms. Expression of 4R/2N in the hippocampus of tau knockin/knockout mice suppresses proliferation and promotes neuronal differentiation (Sennvik et al. 2007). Hyperphosphorylation of tau, particularly in the assembly domain, decreases the affinity of tau to MTs to regulate MT dynamics and axonal transport (Konzack et al. 2007; Dubey et al. 2008). Additional regions in the basic proline-rich domain and the pseudo-repeat also stabilize MTs by interacting with its negatively charged surface (Mukrasch et al. 2007). The projection domain facilitates interaction with the plasma membrane (Brandt et al. 1995; Maas et al. 2000). Interaction of tau with membranes is also thought to facilitate tau aggregation (Chirita et al. 2003). For recent reviews of tau structure and function see (Wang and Liu 2008; Ballatore et al. 2007).

Recent advances in research in AD have highlighted the importance of tau in pathogenesis (Marx, 2007) and its use as a target for the development of disease modifying therapeutics. Evidence from mouse models indicate that reduction of tau expression reverses disease phenotypes (Santacruz et al. 2005; Oddo et al. 2006; Asuni et al. 2007) and that tau is necessary for the development of cognitive deficits in AD models caused by over-expression of Aβ (Roberson et al. 2007). The pathological structures of tau most closely associated with AD progression are tau oligomers in mouse models that also accumulate in human neurodegenerative diseases collectively termed "tauopathies" (Berger et al. 2007; Maeda et al. 2006; Sahara et al. 2007, 2008).

Tau in Neurodegenerative Diseases

Genetic evidence has shown that abnormal forms of tau are sufficient for neurodegeneration causing memory loss and other neurological deficits in multiple frontotemporal dementia and sporadic tauopathies (for a recent review of the role of tau in neurodegeneration see Gendron and Petrucelli 2009; Iqbal et al. 2009). The 32 different mutations found in the study of over 100 families can be grouped into categories influencing splicing of the primary transcript and causing changes in amino acid sequence of tau. Most missense mutations are located in the assembly domain and generally reduce the affinity of tau to MTs. Several of these mutations promote aggregation of tau in vitro and in vivo such as P301L and P301S. Mutations in the stem-loop structure at the border of exon 10 and the following intron alter splicing causing aberrations in the ratio of 4R to 3R isoforms demonstrating that maintenance of the proper ratio of tau isoforms is necessary to prevent neurodegeneration and dementia. Sporadic tauopathies such as progressive supranuclear palsy, corticobasal degeneration, Pick's disease and argyrophilic grain disease are characterized by pathology with tau filaments composed predominantly of 4R isoforms and are linked to MAPT mutations (Goedert and Jakes 2005).

Recent reports also indicate aberrant splicing of tau transcripts in AD demonstrating a common defect with AD and Parkinson disease. Increases in the ratio of 4R to 3R tau mRNAs were found in individual human cholinergic basal forebrain neurons in nucleus basalis and CA1 hippocampal neurons in AD (Ginsberg et al. 2006). Aberrant alternative splicing in sporadic AD was also shown using polymerase colony, a single-molecule-based technology. A trans mechanism involving the reduction of splicing factor htra2-beta-1 in AD was linked to the increase in four-repeat tau isoforms (Conrad et al 2007). Further genetic support for a causative role for tau in AD comes from the observation that tau haplotypes driving higher levels of tau expression increase AD risk (Myers et al. 2005) and from the report of linkage of tau haplotypes with increased CSF tau in people with Aβ deposition accelerated AD progression (Kauwe et al. 2008). Similarly, increased expression of 4R tau and linkage to MAPT haplotypes has been reported for Parkinson disease (Tobin et al. 2008), the second most common form of neurodegenerative disease following AD. A recent study of tau in primary cultures of human cortical neurons indicated that the 4R tau isoforms are principally involved in tau oligomerization (Deshpande et al. 2008). There are also multiple post-translational modifications to tau protein in AD and other tauopathies that cause both loss of function and gain of toxicity (Mazanetz et al., 2007).

In some embodiments, the tau proteins have the following isoforms:

| Residues | Spliced exons | Nomenclature |
|----------|---------------|--------------|
| 352 | — | 3R/0N |
| 381 | 3 | 3R/1N |
| 410 | 2, 3 | 3R/2N |
| 383 | 10 | 4R/0N |
| 412 | 3, 10 | 4R/1N |
| 441 | 2, 3, 10 | 4R/2N |

Recent advances in research in AD have highlighted the importance of tau in pathogenesis (Marx, 2007) and its use as a target for the development of disease modifying therapeutics. Evidence from mouse models indicate that tau reduction reverses disease phenotypes (Santacruz et al. 2005; Oddo et al. 2006; Asuni et al. 2007) and that tau is necessary for the development of cognitive deficits in AD models caused by over-expression of Aβ (Roberson et al. 2007).

The pathological structures of tau most closely associated with AD progression are tau oligomers in mouse models that also accumulate in human neurodegenerative diseases collectively termed "tauopathies" (Berger et al. 2007; Maeda et al. 2006; Sahara et al. 2007, 2008). NFTs have been implicated in mediating neurodegeneration in AD and tauopathies as it correlates well with cognitive deficits and neuron loss (Arriagada et al., 1992; Bancher 1993; Guillozet et al., 2003; Iqbal et al. 2009). However, the study of animal models of tauopathy has shown that memory impairment and neuron loss is dissociated from accumulation of NFT (Brunden et al. 2008; Rocher et al. 2009). Strong support for this contention came from the analysis of transgenic mice rTg4510 that express tau P301L in the forebrain under control of a tetracycline-regulated promoter. These mice developed memory impairment, neuron loss and NFT when the construct was expressed.

However, suppression of expression caused improvement in memory and reduction in neuron loss even as NFTs continued to accumulate clearly demonstrating that pretangle tau species were responsible for the neurodegenerative phenotype (Santacruz et al. 2005). Additionally, there was regional dissociation of neuron loss and NFT pathology in this model (Spires et al. 2006) and in another mouse model expressing all six human isoforms (Andorfer et al. 2003) showing that tangles are not acutely neurotoxic.

Incongruence between tangle formation, neurodegeneration and behavioral deficits were found in other mouse models of tauopathy and AD. Transgenic mice expressing a human mutant tau P3015 construct prone to aggregation developed hippocampal synapse loss and dysfunction, as well as, microglial activation months before the accumulation of filamentous tau inclusions (Yoshiyama et al. 2007). Similarly, a transgenic mouse model expressing human tau protein with two mutations found in FTDP-17 (P301S and G272V) exhibited axonopathy before tangle formation (Leroy et al. 2007). The triple transgenic AD mouse model accumulating both tau and Aβ pathology was used to study the effects of immuno-reduction of tau and Aβ. Antibodies against both proteins were needed to improve learning and memory behavior in these mice. Soluble tau, but not NFT, was reduced by the treatment again showing the dissociation between the neurodegenerative phenotype and insoluble tau aggregates (Oddo et al. 2006).

Extracellular Tau in Disease Progression

Contiguous spread of tau pathology is a hallmark of AD. Tau pathology progresses through anatomically adjacent areas from the hippocampus through the cortex in early to mild AD From early stages to later stages, the disease spreads contiguously throughout the brain. As AD progresses, tau pathology engulfs the hippocampal structure in a highly selective and orderly fashion (Schonheit B. et al. 2004).

The role of extracellular tau in neurotoxicity is a relatively new but important concept in the field. There are a number of contributing findings that implicate extracellular tau in AD. Levels of tau rise in CSF in AD, whereas Aβ levels decrease (Shaw et al. 2009). Work in progress at OLIGOMERIX, Inc. also shows that tau oligomers accumulate progressively in CSF of AD patients (Davidowitz et al. 2008a). Tau pathology spreads contiguously throughout the brain from early to late stage disease suggesting an "infectious" model of disease progression (Schonheit et al. 2004). This notion is supported by a recent report (Frost et al. 2009) that extracellular tau aggregates can propagation tau misfolding from the outside to the inside of a cell. Additional backing for this concept comes from a recent report showing that injection of brain extract from a transgenic mouse with aggregated mutant human tau into the brain of transgenic mice with normal human tau transmits tau pathology and induces its spread throughout the brain (Clavaguera et al., 2009, in press). In neurons of transgenic mice Induction of low levels of pro-aggregation human tau results in the formation of tau aggregates and tangles composed of both human and normal murine tau (co-aggregation) providing evidence for the "infectious" model by transmission of pathological tau characteristics to normal host tau (Mocanu et al. 2008). A receptor-mediated mechanism for the spread of tau pathology by extracellular tau has been described based on work with cultured neurons (Gomez-Ramos et al. 2006, 2008, 2009).

Proposed Models for Tau Aggregation

Models have been proposed to explain pathways of tau self-interaction leading to dimer formation and higher order oligomer and fibril structures. Congdon et al. (2008) presents a model in which there are four principal steps for tau assembly into fibrils that are: 1.) tau dissociation from microtubules leading to increase in its cytosolic concentration; 2.) conformational change to enable aggregation 3.) dimerization/nucleation, the rate-limiting step in fibrillization; and 4.) fibril elongation by addition of monomeric tau. In this model disulfide bond formation and orientation of tau molecules are not addressed.

The Mandelkow laboratory (Schweers et al. 1995; Friedhoff et al. 1998) proposed a model in which the first step is tau dimerization by formation of disulfide bonds. Tau molecules in the dimers are arranged in an antiparallel fashion and serves as a template for further elongation by dimer addition. In this model there are no disulfide bonds between dimers. Formation of intramolecular disulfide linkages in 4R tau form compact monomers that cannot nucleate tau assembly. Anions such as heparin are thought to neutralize the basic charge of the assembly domain to enhance tau self-interaction and found to accelerate tau assembly in the absence of disulfide bond formation. The hydrophobic hexa-peptide motifs in R2 and R3 stabilize the aggregates and salt bridges are the major stabilizing elements of PHFs one they are formed (Jeganathan et al. 2008).

Dynamic light scattering studies were used to study aggregation of tau 3R and 4R microtubule binding domains (MBD), and different models were proposed for the initial aggregation pathways of these constructs (Sugino et al. 2009). Intramolecular disulfide bonds form in 4R tau between the cysteines of the second and third repeats in monomeric 4R tau in a non-reducing environment. These monomers interact to form noncovalent dimers driven by hydrophobic interactions of amphipathic amino acid sequences in the third repeat. Anti-parallel stacking of the dimers leads to formation of fibrils. The tau 3R assembly domain forms covalent anti-parallel dimers, driven by intermolecular disulfide bond formation that orients the amphipathic regions in the third repeat for hydrophobic interactions, that stack to form fibrils (Sugino et al. 2009). This model is similar to the one developed in the Mandelkow laboratory for 3R tau but differs on the point that 4R tau constructs with intramolecular disulfide bridges can nucleate filament formation (Schweers et al. 1995).

A colloidal aggregation model for amyloid fiber formation was reported (Xu 2007) for amyloidogenic proteins in which they aggregate and form nucleation units driven by surface energy minimization. The nucleation units may have an intrinsic dipole moment originating from an asymmetric charge distribution facilitating colloidal aggregation to form linear fibers. Granular tau oligomers can be formed in vitro in the presence of heparin polyanions under non-reducing conditions (Maeda et al. 2006, 2007). Using this approach, granular aggregates of 40-74 tau molecules first formed before fusing to form filaments. This process was reversible suggesting this pathway may yield filaments that differ from PHFs (Congdon et al. 2008). Anionic detergent was used to isolate granular tau aggregates from AD brain specimens, but their morphology could not distinguish whether they represented small filaments or micellar aggregates (Maeda et al. 2006).

Here, we propose a novel model for tau oligomerization that provides novel compositions of tau oligomers that help teach how the relative overexpression of 4R tau can facilitate tau aggregation and neurodegenerative disease and how these structures may be used for discovery of small molecule drugs, immunotherapeutics and biomarkers for neurodegenerative diseases.

Having now generally described the invention, the same may be more readily understood through the following reference to the following examples, which are provided by way of illustration and are not intended to limit the present invention unless specified.

EXAMPLE

Example 1

Figure 6:
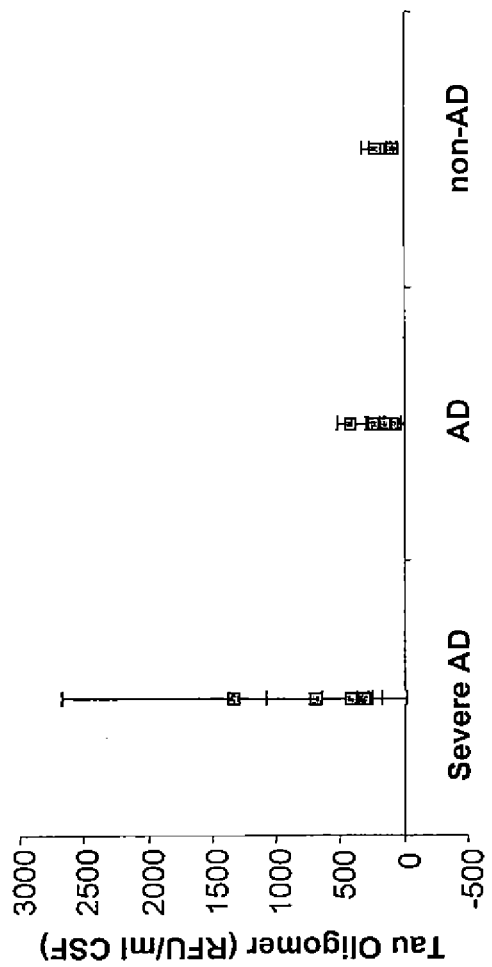
FIG. 6 illustrates that tau-oligomer levels in CSF accumulate progressively during disease as determined by an oligomer conformation-specific ELISA using capture antibody against tau c-terminus. The subset of tau oligomers containing tau with an intact c-terminus was studied using capture antibody mAb T46, specific for the 37 carboxyl terminal amino acids of tau, to improve the resolution of non-AD, moderate AD and severe AD samples in combination with detection antibody pAb A11.

A tau oligomer conformation ELISA (—COOH terminal capture) was conducted to determine tau oligomer levels in CSF from severe AD, AD and non-AD patients (specimens provided by New York Brain Bank, Taub Center, Columbia University Medical Center). The capture antibody used was mAb T46 that specifically binds to the 37 c-terminal amino acids of tau. The reporter antibody was pAb A11, specific for tau oligomer conformation. Patient samples were analyzed (4 with severe AD, 4 patients with AD and 3 patients having no AD as diagnosed by autopsy). The results in FIG. 6 from testing the sample with the assay clearly show that there is a substantial difference, as measured by fluorescence units, between patients with non-AD and severe AD. Thus, this assay format can be used as a biomarker to diagnose AD from non-AD (e.g., determine the presence or absence of AD) or stratify or monitor the progression or regression of AD (shown in FIG. 6).

Example 2

Figure 7:
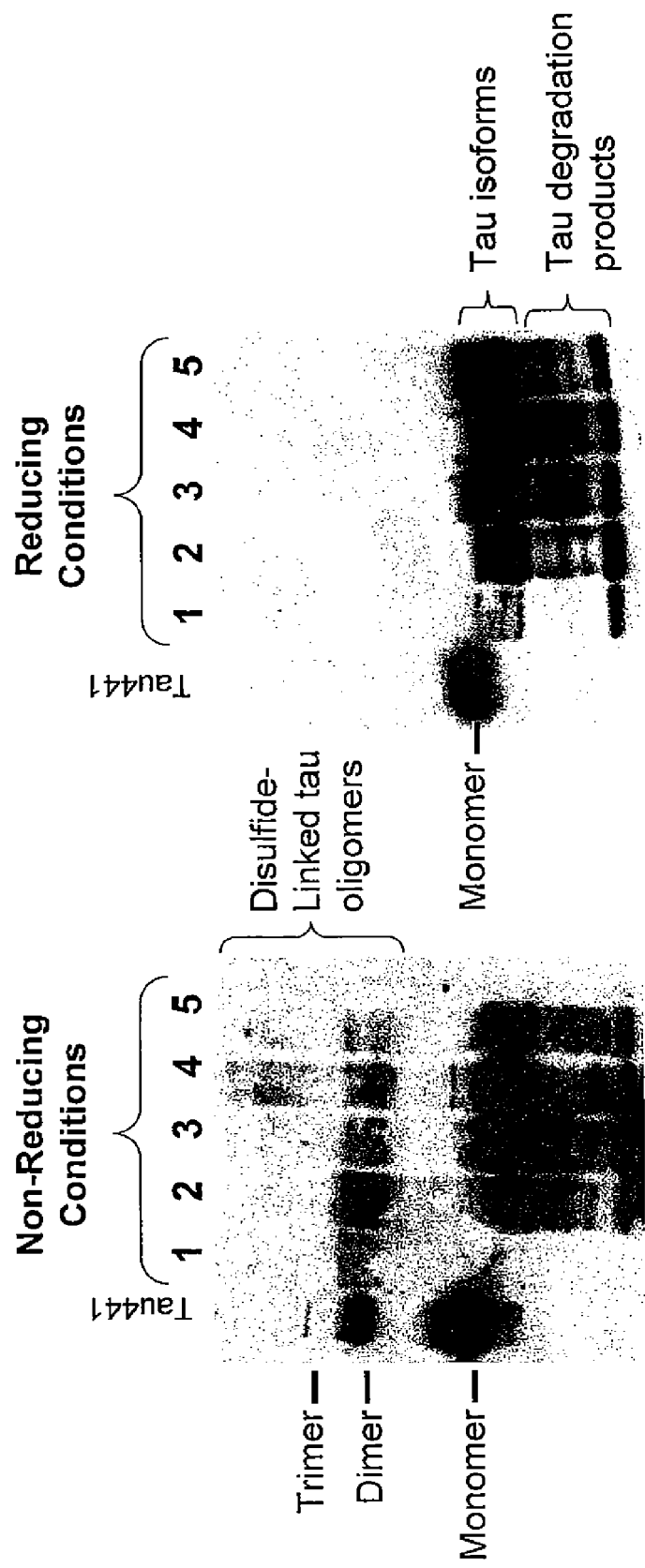
FIG. 7 illustrates that disulfide-linked tau oligomers are present in the cerebrospinal fluid (CSF) of AD patients illustrating the biological relevance of extracellular disulfide-linked tau oligomers.

Five post-mortem CSF specimens (10 µl each) from individuals with advanced AD were analyzed by SDS PAGE using a 4-20% gradient gel (BioRad). Specimens were provided by New York Brain Bank, Taub Center, Columbia University Medical Center. Samples were prepared with standard Laemmli buffer (sample buffer containing reductant) or sample buffer without reductant. Proteins were transferred to a nitrocellulose membrane and immunoblot was performed with mAb HT7 recognizing all tau isoforms and independently of tau phosphorylation (shown in FIG. 7).

Example 3

Figure 8:
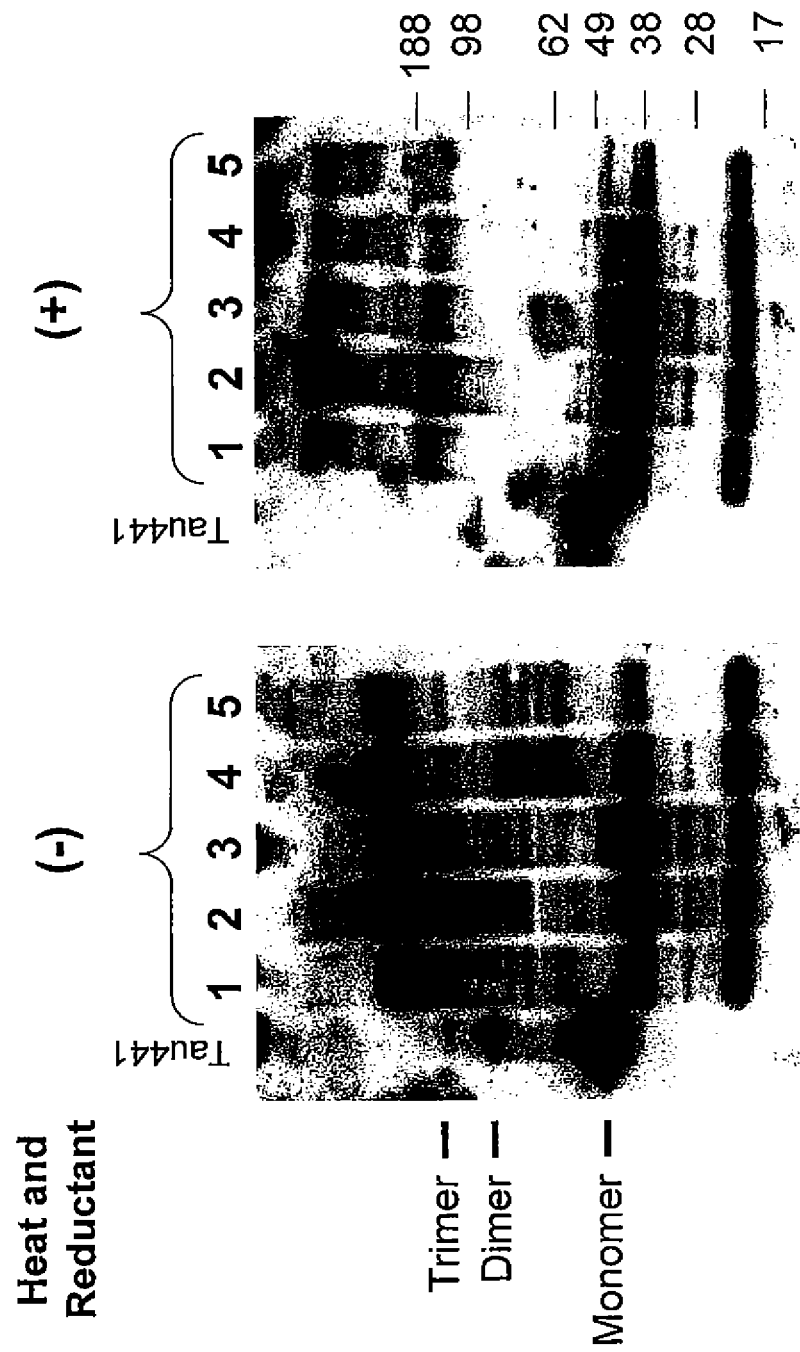
FIG. 8 illustrates that tau in CSF is "reactive" in that it contains reactive thiols and forms higher order aggregates if accelerated by temperature elevation as shown in the left panel. The panel on the right shows the higher order aggregates that are stable to reducing conditions, SDS, and heat.

Five post-mortem CSF specimens (15 µg each) from individuals with advanced AD were analyzed by SDS PAGE using a 4-20% gradient gel (BioRad). Samples were prepared with standard sample buffer containing reductant or sample buffer without reductant. Specimens were provided by New York Brain Bank, Taub Center, Columbia University Medical Center. The samples with reductant were heated 5 min at 95° C. before loading on gel. Proteins were transferred to a nitrocellulose membrane and immunoblot was performed with mAb HT7 recognizing all tau isoforms and independently of tau phosphorylation (shown in FIG. 8).

Example 4

Figure 9:
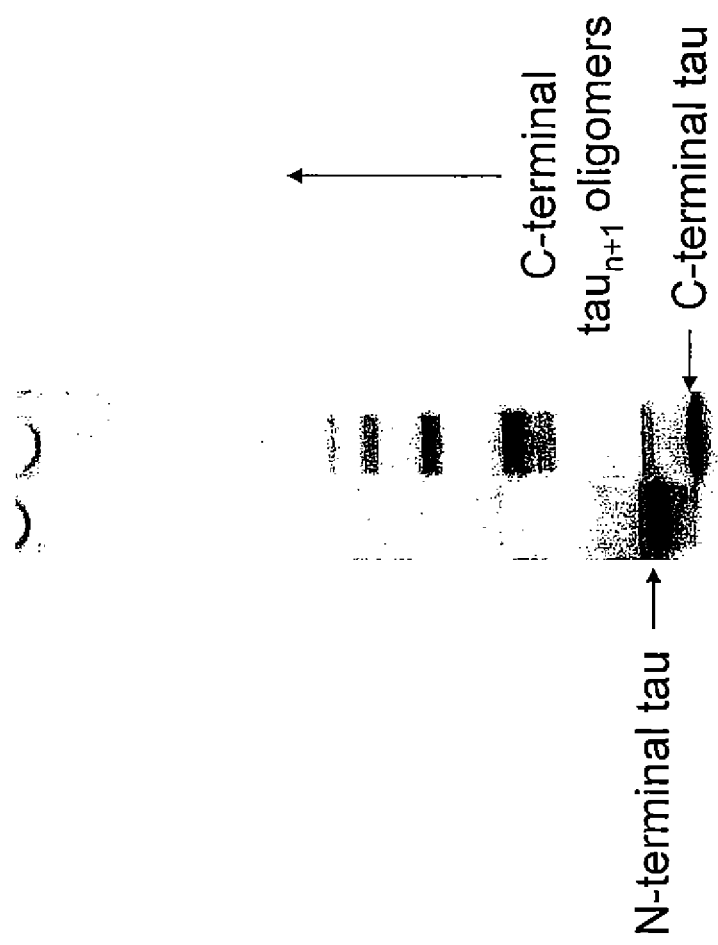
FIG. 9 illustrates 4R tau oligomer formation is driven by the microtubule binding domain in the C-terminus. A tau fragment (18.5 KD) that encompasses the C-terminus is able to oligomerize (charge approximately +13.2) whereas a tau fragment (21.5 KD) that encompasses the N-terminus does not form any significant higher order structures (charge approximately −7.2). Shown in lane 1 is the MW ladder, lane 2 tau441 monomer, lane 3 Tau441 oligomer mixture, lane 4, the N-terminal portion of tau protein (amino acids 1-184)

Protein preparations of the N-terminal (21.5 kDa) and C-terminal (18.5 kDa) were incubated at 4 µM concentration in pH neutral buffer and incubated overnight at 37° C. SDS-PAGE using a 4-20% gradient gel (BioRad) was used to resolve the oligomeric species (shown in FIG. 9).

Example 5

Recombinant human Tau441 protein was expressed in bacteria using standard methods and purified using cation exchange with SP Sepharose and size fractionation using continuous gel electrophoresis (BioRad). The protein was incubated at 1 mg/ml in 50 mM Tris-Hcl pH 7.4. SDS-PAGE using a 4-20% gradient gel (BioRad) was used to resolve the oligomeric species. Silver staining was performed with the Silver Express kit (Invitrogen) (shown in FIG. 10).

Example 6

Recombinant human Tau412 protein was expressed in bacteria using standard methods and purified using cation exchange with SP Sepharose and size fractionation using continuous gel electrophoresis (BioRad). The protein was incubated at 1 mg/ml in 50 mM Tris-HCl pH 7.4 and 1 mg of the oligomerized preparation was used for purification of individual oligomers using continuous gel electrophoresis (BioRad). Non-reducing sample buffer was used to prepare samples for SDS-PAGE using a 4-20% gradient gel (BioRad) to resolve purified tau monomer, dimer, trimer and tetramer. Silver staining was performed with the Silver Express kit (Invitrogen) (shown in FIG. 11).

Example 7

Aliquots of purified tau441 dimer and trimer preparation were incubated in buffer (Tris-HCl pH 7.4) for 1 hr. at 10, 20, 30, 40, 50, 60 70, 80 or 90° C. in a thermal block with a heated lid for 10 min. Non-reducing sample buffer was used to prepare samples for SDS-PAGE using a 4-20% gradient gel (BioRad) to resolve purified tau monomer, dimer, trimer and tetramer. Silver staining was performed with the Silver Express kit (Invitrogen) (shown in FIG. 12).

Example 8

Tau441 dimer and timer aliquots were incubated in 1×Tris/glycine/SDS running buffer with no NaCl, 100 mM or 200 mM NaCl for either 15 or 60 minutes. SDS-PAGE using a 4-20% gradient gel (BioRad) was used to resolve the protein in the samples. Non-reducing sample buffer was used to prepare samples for SDS-PAGE using a 4-20% gradient gel (BioRad) to resolve purified tau monomer, dimer, trimer and tetramer. Silver staining was performed with the Silver Express kit (Invitrogen) (shown in FIG. 13).

Example 9

Purified dimer and trimer tau441 aliquots were incubated with or without 50 mM DTT for 15, 30 or 60 min. at 37° C. Non-reducing sample buffer was used to prepare samples for SDS-PAGE using a 4-20% gradient gel (BioRad) to resolve purified tau monomer, dimer, trimer and tetramer. Silver staining was performed with the Silver Express kit (Invitrogen) (shown in FIG. 14).

Example 10

Purified preparations of tau352 or tau441 were incubated at 37° C. in neutral buffer with a very low concentration of hydrogen peroxide to create an oxidizing environment that would not lead to protein degradation. Non-reducing sample buffer was used to prepare samples for SDS-PAGE using a 4-20% gradient gel (BioRad) to resolve purified tau monomer, dimer, trimer and tetramer. Silver staining was performed with the Silver Express kit (Invitrogen) (shown in FIG. 15).

Example 11

Purified preparations of tau352 and tau441 were incubated at a 1:1 ratio or 1:4 ratio of tau352:tau441 at 37° C. in pH neutral buffer for 45 min. or 2 days. Non-reducing sample buffer was used to prepare samples for SDS-PAGE using a 4-20% gradient gel (BioRad) to resolve purified tau monomer, dimer, trimer and tetramer. Silver staining was performed with the Silver Express kit (Invitrogen) (shown in FIG. 19).

The references below are hereby incorporated in the present disclosure for all that they disclose.

REFERENCES

Amos L A. Microtubule structure and its stabilisation. Org Biomol Chem. 2004, 2(15):2153-60.

Andorfer C, Kress Y, Espinoza M, de Silva R, Tucker K L, Barde Y A, Duff K, Davies P. Hyperphosphorylation and aggregation of tau in mice expressing normal human tau isoforms. J Neurochem. 2003, 86(3):582-90.

Arriagada, P. V., Growdon, J. H., Hedley-Whyte, E. T., and Hyman, B. T. Neurofibrillary tangles but not senile plaques parallel duration and severity of Alzheimer's disease. 1992, Neurology, 42(3 Pt 1), 631.

Asuni A A, Boutajangout A, Quartermain D, Sigurdsson E M. Immunotherapy targeting pathological tau conformers in a tangle mouse model reduces brain pathology with associated functional improvements. J Neurosci. 2007, 27(34):9115-29.

Ballatore C, Lee V M, Trojanowski J Q. Tau-mediated neurodegeneration in Alzheimer's disease and related disorders. Nat Rev Neurosci. 2007, 8(9):663-72.

Bancher, C., Braak. H., Fischer, P., and Jellinger, K. A. Neuropathological staging of Alzheimer lesions and intellectual status in Alzheimer's and Parkinson's disease patients. 1993, Neurosci. Lett., 162, 179.

Berger Z, Roder H, Hanna A, Carlson A, Rangachari V, Yue M, Wszolek Z, Ashe K, Knight J, Dickson D, Andorfer C, Rosenberry T L, Lewis J, Hutton M, Janus C. Accumulation of pathological tau species and memory loss in a conditional model of tauopathy. J Neurosci. 2007, 27(14):3650-62.

Brandt R, Leger J, Lee G. Interaction of tau with the neural plasma membrane mediated by tau's amino-terminal projection domain. J Cell Biol. 1995 December; 131(5):1327-40.

Brunden K R, Trojanowski J Q, Lee V M. Evidence that non-fibrillar tau causes pathology linked to neurodegeneration and behavioral impairments. J Alzheimers Dis. 2008, 14(4):393-9.

Chirita C N, Necula M, Kuret J. Anionic micelles and vesicles induce tau fibrillization in vitro. J Biol Chem. 2003, 278(28):25644-50.

Clavaguera F, Bolmont T, Crowther R A, Abramowski D, Frank S, Probst A, Fraser G, Stalder A K, Beibel M, Staufenbiel M, Jucker M, Goedert M, Tolnay M. Transmission and spreading of tauopathy in transgenic mouse brain. Nat Cell Biol. 2009, 11(7):909-13.

Congdon E E, Kim S, Bonchak J, Songrug T, Matzavinos A, Kuret J. Nucleation-dependent tau filament formation: the importance of dimerization and an estimation of elementary rate constants. J Biol Chem. 2008, 283(20):13806-16.

Conrad C, Zhu J, Conrad C, Schoenfeld D, Fang Z, Ingelsson M, Stamm S, Church G, Hyman B T. Single molecule profiling of tau gene expression in Alzheimer's disease. J Neurochem. 2007, 103(3):1228-36.

Davidowitz E J, Chatterjee I, Moe J G. Targeting tau oligomers for therapeutic development for Alzheimer's disease and tauopathies. Current Topics in Biotechnology 2008 4:47-64.

Deshpande A, Win K M, Busciglio J. Tau isoform expression and regulation in human cortical neurons. FASEB J. 2008, 22(7):2357-67.

Dubey M, Chaudhury P, Kabiru H, Shea T B. Tau inhibits anterograde axonal transport and perturbs stability in growing axonal neurites in part by displacing kinesin cargo: neurofilaments attenuate tau-mediated neurite instability. Cell Motil Cytoskeleton. 2008, 65(2):89-99.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A composition comprising a non-naturally occurring purified and/or isolated and stabilized tau oligomer and a buffer, wherein the tau oligomer comprises human recombinant tau protein produced recombinantly from bacteria in a buffer having a neutral pH, the tau oligomer being in a trimeric form having a first tau monomer containing a first cysteine, a second tau monomer containing a second cysteine, and a third tau monomer containing a third cysteine, wherein the first tau monomer is covalently attached to the second tau monomer and the second tau monomer is covalently attached to the third tau monomer by an intermolecular disulfide linkage between at least the first cysteine, the second cysteine and the third cysteine, and each monomer has an N-terminal and a C-terminal in a parallel orientation relative to each other in the trimeric form, and the tau oligomer is at least 90% purified, wherein the tau oligomer is formed without the addition of heparin or other polyanions.

2. A composition according to claim 1, wherein (i) the tau monomeric unit comprises one of SEQ ID NO. 1-6; or (ii) the tau oligomer is stable for at least 2 months.

3. A composition according to claim 2, wherein each monomer has a peptide backbone with an N-terminal and C-terminal substantially parallel to each other in the trimeric form and the first tau monomer is covalently attached to the second tau monomer by an intermolecular disulfide linkage between an R2 cysteine 291 from the first tau monomer of SEQ ID NO. 6 and the R3 cysteine 322 from the second tau monomer of SEQ ID NO. 6.

4. A composition according to claim 2, wherein the tau oligomer has a free thiol group from each monomer, one from an R2 cysteine on the first tau monomer and one from an R3 cysteine on the second tau monomer.

5. A composition according to claim 2, wherein the tau oligomer has microtubule binding regions and said regions are aligned out of phase such that R2 and R3 regions are able to bind via formation of cross beta sheet interaction and the disulfide linkage.

6. A composition comprising tau oligomers according to claim 1, wherein the tau oligomers are formed by bonding a tau dimer with a tau monomer to form tau trimer, wherein the dimer is selected from tau 4R dimer and tau 4R/3R dimer, and the tau monomer is selected from tau 4R monomer and tau 3R monomer.

7. A composition according to claim 1, wherein the purified and stabilized tau oligomer is capable of generating antibodies that bind specifically to the purified and stabilized tau oligomer when administered to a mammal.

8. A composition according to claim 1, wherein the purified and stabilized tau oligomer comprises an aggregation core between an R2 and R3 region of two separate tau peptides, said tau peptides having no free thiol moieties.

9. A composition according to claim 1, wherein the purified and stabilized tau oligomer comprises tau oligomers bound by disulfide linkages between R2 and R3 regions of tau oligomers or R3 and R3 regions of tau oligomers and the composition is capable of being used in a screening assay to screen drug compounds that enhance or inhibit tau oligomer formation.

10. A composition according to claim 9, wherein the drug compounds prevents or inhibits tau-tau binding resulting from hydrogen bonding, van der Waals interaction such that disulfide bond formation is blocked or prevented.

11. A composition according to claim 1, wherein the purified and stabilized tau oligomer comprises tau oligomers bound by disulfide linkages between R2 and R3 regions of tau oligomers or R3 and R3 regions of tau oligomers.

12. A composition according to claim 1, wherein each monomer comprises an N-terminal and a C-terminal in a parallel orientation relative to each other in the trimeric form.

13. A composition according to claim 1, wherein the tau oligomer is isolated and/or purified with a buffering agent comprising magnesium hydroxide, aluminum hydroxide, alginic acid, pyrogen-free water, isotonic saline, Ringer's solution, ethyl alcohol or phosphate buffer solutions.

14. A composition according to claim 1, wherein tau oligomer size is controlled by modulating the ratio of 3R:4R tau concentrations.

15. A composition according to claim 1, wherein the tau oligomer is at least 95%, at least 98% or at least 99% purified.

16. A composition according to claim 1, wherein the tau oligomer comprises at least a first tau monomer that is in a 4R conformation and a second tau monomer that is in a 4R conformation, wherein each monomer comprises an N-terminal and a C-terminal and is in a parallel orientation relative to each other and the tau oligomer is in a tau trimer.

17. A composition according to claim 1, wherein the tau oligomer is in a phosphate buffer.

18. A composition according to claim 17, wherein the buffer is a Tris buffer.

19. A composition according to claim 1, wherein the composition is used to screen for disrupted tau oligomer.

20. A composition according to claim 1, wherein the tau oligomer is formed without a reducing agent.

21. A composition according to claim 1, wherein a fragment of the tau oligomer is useful as a target for an antibody fragment.

22. A composition comprising a non-naturally occurring isolated, substantially purified and stabilized tau oligomer and a buffer, wherein the tau oligomer comprises human recombinant tau protein recombinantly produced from bacteria in a buffer having a neutral pH, wherein the tau oligomer is in at least a trimeric form having a first tau monomer containing a first cysteine and a second tau monomer containing a second cysteine, wherein the first tau monomer is covalently attached to the second tau monomer by an intermolecular disulfide linkage between at least the first cysteine and the second cysteine and is used as an immunotherapeutic agent, and the isolated, substantially purified and stabilized tau oligomer is used for passive or active immunotherapy and is at least 90% purified, wherein the tau oligomer is formed without the addition of heparin or other polyanions.

23. A composition comprising a non-naturally occurring purified and/or isolated and stabilized tau oligomer and a buffer, wherein the tau oligomer comprises human recombinant tau protein produced recombinantly from bacteria in a buffer, the tau oligomer having a first tau monomer containing one or two cysteines, a second tau monomer containing two cysteines, and a third tau monomer containing one or two cysteines, wherein the first tau monomer is covalently attached to the second tau monomer and the second tau monomer is covalently attached to the third tau monomer by intermolecular disulfide linkages, and each monomer has a parallel N-terminal to C-terminal orientation relative to each other in the trimeric form, and the tau oligomer is at least 90% purified, wherein the tau oligomer is formed without the addition of heparin or other polyanions.

24. A composition comprising a non-naturally occurring isolated, substantially purified and stabilized tau oligomer and a buffer, wherein the tau oligomer comprises human recombinant tau protein produced recombinantly from bacteria in a buffer, wherein the tau oligomer is in at least a trimeric form having a first tau monomer containing one or two cysteines, a second tau monomer containing two cysteines, and a third tau monomer containing one or two cysteines, wherein the first tau monomer is covalently attached to the second tau monomer and the second tau monomer is covalently attached to the third tau monomer by intermolecular disulfide linkages, and each monomer has a parallel N-terminal to C-terminal orientation relative to each other in the trimeric form, wherein the tau oligomer is at least 90% purified and is formed without the addition of heparin or other polyanions, and the composition is used as an immunotherapeutic agent for passive or active immunotherapy.

25. A composition comprising tau oligomers according to claim 23, wherein the tau oligomers are formed by bonding a tau dimer with a tau monomer to form tau trimer, wherein the dimer is selected from tau 4R dimer and tau 4R/3R dimer, and the tau monomer is selected from tau 4R monomer and tau 3R monomer.

26. A composition according to claim 23, wherein the tau oligomers are produced from recombinant bacteria in a neutral pH.

* * * * *